(12) United States Patent
LeGette et al.

(10) Patent No.: US 7,617,543 B2
(45) Date of Patent: Nov. 17, 2009

(54) APPARATUS AND METHOD FOR MAKING AN EAR WARMER AND AN EAR WARMER FRAME

(75) Inventors: Brian Edward LeGette, Baltimore, MD (US); Justin Saul Werner, Millersville, MD (US); Ronald L. Wilson, II, Catonsville, MD (US)

(73) Assignee: 180s, Inc., Baltimore, MD (US)

( * ) Notice: Subject to any disclaimer, the term of this patent is extended or adjusted under 35 U.S.C. 154(b) by 205 days.

(21) Appl. No.: 11/759,002

(22) Filed: Jun. 6, 2007

(65) Prior Publication Data

US 2007/0220657 A1    Sep. 27, 2007

Related U.S. Application Data

(63) Continuation of application No. 11/619,424, filed on Jan. 3, 2007, which is a continuation of application No. 11/108,615, filed on Apr. 18, 2005, now abandoned, which is a continuation of application No. 10/335,930, filed on Jan. 3, 2003, now Pat. No. 6,920,645, which is a continuation of application No. 09/986,103, filed on Nov. 7, 2001, now Pat. No. 6,502,248, which is a continuation of application No. PCT/US01/11041, filed on Apr. 5, 2001, which is a continuation-in-part of application No. 09/521,241, filed on Apr. 5, 2000, now Pat. No. 6,332,223.

(51) Int. Cl.
*A42B 1/06* (2006.01)
(52) U.S. Cl. .......................................................... 2/209
(58) Field of Classification Search .................... 2/209, 2/183; 128/864; 381/383
See application file for complete search history.

(56) References Cited

U.S. PATENT DOCUMENTS

| | | | |
|---|---|---|---|
| 138,894 A | 5/1873 | Isidor |
| 139,831 A | 6/1873 | Stone |
| 183,359 A | 10/1876 | Abbott |
| 185,506 A | 12/1876 | Edgar |
| 188,292 A | 3/1877 | Greenwood |
| 359,612 A | 3/1887 | Kleinert |
| 360,985 A | 4/1887 | Basch |
| 365,061 A | 6/1887 | Friedman |

(Continued)

FOREIGN PATENT DOCUMENTS

CA    2180036    1/1997

(Continued)

OTHER PUBLICATIONS

Advertisement: The "PODZ" ear warming eye glass retainer, Shred Alert Products of Hood River, Oregon, 5 pgs.

(Continued)

*Primary Examiner*—Katherine Moran
(74) *Attorney, Agent, or Firm*—Edell, Shapiro & Finnan LLC

(57) ABSTRACT

An ear warmer comprises a set of membranes and a frame. The set of membranes collectively defines an outer perimeter. The set of membranes is attached along the outer perimeter to define an attachment portion. The attachment portion is entirely disposed within an interior of the set of membranes. The frame is disposed within the interior of the set of membranes

19 Claims, 18 Drawing Sheets

U.S. PATENT DOCUMENTS

| | | |
|---|---|---|
| 375,594 A | 12/1887 | Basch |
| 381,559 A | 4/1888 | Kleinert et al. |
| 503,703 A | 8/1893 | Kleinert |
| 529,176 A | 11/1894 | Kleinert |
| 548,738 A | 10/1895 | Ballard |
| 804,731 A | 11/1905 | Keller |
| 836,087 A | 11/1906 | Callahan |
| 869,741 A | 10/1907 | Seitzman |
| 932,487 A | 8/1909 | Melio |
| 953,623 A | 3/1910 | Keller |
| 1,167,368 A | 1/1916 | Adams-Randall |
| 1,179,473 A | 4/1916 | Taylor |
| 1,274,842 A | 8/1918 | Basch |
| 1,326,875 A | 12/1919 | Miller |
| 1,398,958 A | 12/1921 | Basch |
| 1,567,105 A | 12/1925 | Bohlman |
| 1,577,183 A | 3/1926 | Dowiarz |
| 1,628,483 A | 5/1927 | Wiegand et at |
| 1,988,880 A | 1/1935 | Strouse |
| 2,070,216 A | 2/1937 | Rosenberg |
| 2,120,189 A | 6/1938 | Reinemer |
| 2,149,383 A | 3/1939 | Bean |
| 2,216,954 A | 10/1940 | McDonough |
| 2,246,031 A | 6/1941 | Baritz et al |
| 2,314,782 A | 3/1943 | Goretsky |
| 2,333,392 A | 11/1943 | Rosenzweig |
| 2,378,398 A | 6/1945 | Fiedler |
| 2,405,326 A | 8/1946 | Plotsky |
| 2,420,245 A | 5/1947 | Hurst |
| 2,437,049 A | 3/1948 | Salisbury et at |
| 2,532,852 A | 12/1950 | Oaks |
| 2,582,907 A | 1/1952 | Kaufmann |
| 2,586,644 A | 2/1952 | Gilbert |
| 2,615,169 A | 10/1952 | Maxant |
| 2,651,046 A | 9/1953 | Berg |
| 2,671,221 A | 3/1954 | Triplett |
| 2,717,930 A | 9/1955 | Hintz |
| 2,776,436 A | 1/1957 | Berg |
| 2,782,423 A | 2/1957 | Simon et al. |
| 2,858,544 A | 11/1958 | Roth |
| 2,899,683 A | 8/1959 | Wadsworth et at |
| 2,946,860 A | 7/1960 | Jansen et al |
| 3,087,028 A | 4/1963 | Bonnin |
| 3,104,398 A | 9/1963 | Palmaer |
| 3,112,493 A | 12/1963 | Greenberg |
| 3,119,119 A | 1/1964 | Millinger et al |
| 3,119,904 A | 1/1964 | Anson |
| 3,156,923 A | 11/1964 | Timm |
| 3,249,949 A | 5/1966 | Rosenberg et al |
| 3,308,480 A | 3/1967 | Elder |
| 3,311,713 A | 3/1967 | Knuebel |
| 3,440,663 A | 4/1969 | Beguin |
| 3,447,160 A | 6/1969 | Teder |
| 3,509,580 A | 5/1970 | Rubenstein et al. |
| 3,721,993 A | 3/1973 | Lonnstedt |
| 3,728,741 A | 4/1973 | Lepor |
| 3,787,899 A | 1/1974 | Krawagna |
| 3,841,325 A | 10/1974 | Pickard |
| 3,944,018 A | 3/1976 | Satory |
| 4,048,453 A | 9/1977 | Seidel |
| 4,065,176 A | 12/1977 | Fontana |
| 4,133,053 A | 1/1979 | Lundin |
| 4,277,847 A | 7/1981 | Florio |
| 4,349,081 A | 9/1982 | Pepple |
| 4,391,000 A | 7/1983 | Lonnstedt |
| 4,404,434 A | 9/1983 | Pelt et al. |
| 4,409,442 A | 10/1983 | Kamimura |
| 4,445,005 A | 4/1984 | Furuhashi |
| 4,455,457 A | 6/1984 | Akira |
| 4,463,223 A | 7/1984 | Yamanoi et al. |
| 4,471,496 A | 9/1984 | Gardner, Jr. et al. |
| 4,486,903 A | 12/1984 | Krystal |
| 4,499,593 A | 2/1985 | Antle |
| 4,516,274 A | 5/1985 | Buckland |
| 4,542,803 A | 9/1985 | Houng |
| 4,546,215 A | 10/1985 | Ferraro |
| 4,571,746 A | 2/1986 | Gorike |
| 4,609,786 A | 9/1986 | Omoto et al. |
| 4,615,185 A | 10/1986 | Bollinger |
| 4,633,530 A | 1/1987 | Satterfield |
| 4,654,898 A | 4/1987 | Ishikawa |
| 4,660,229 A | 4/1987 | Harris |
| 4,662,590 A | 5/1987 | Hungerford, Jr. |
| 4,669,129 A | 6/1987 | Chance |
| 4,670,911 A | 6/1987 | Dunford |
| 4,682,374 A | 7/1987 | Geiser |
| 4,713,843 A | 12/1987 | Duncan |
| 4,727,599 A | 2/1988 | Rappaport et al. |
| 4,747,145 A | 5/1988 | Wiegel |
| 4,776,042 A | 10/1988 | Hanson et al. |
| 4,776,044 A | 10/1988 | Makins |
| 4,783,822 A | 11/1988 | Toole et al. |
| 4,791,684 A | 12/1988 | Schwartz |
| 4,796,307 A | 1/1989 | Vantine |
| 4,802,245 A | 2/1989 | Miano |
| D301,477 S | 6/1989 | Storyk |
| 4,858,248 A | 8/1989 | Goldsmith et al. |
| 4,864,619 A | 9/1989 | Spates |
| 4,872,219 A | 10/1989 | Duncan |
| 4,907,266 A | 3/1990 | Chen |
| 4,918,757 A | 4/1990 | Janssen et al. |
| 4,982,451 A | 1/1991 | Graham |
| 5,003,589 A | 3/1991 | Chen |
| 5,033,094 A | 7/1991 | Hung |
| 5,038,412 A | 8/1991 | Cionni |
| 5,046,192 A | 9/1991 | Ryder |
| 5,052,194 A | 10/1991 | Jarus |
| 5,086,789 A | 2/1992 | Tichy |
| 5,117,464 A | 5/1992 | Jones et al. |
| 5,117,465 A | 5/1992 | MacDonald |
| 5,164,987 A | 11/1992 | Raven |
| 5,201,856 A | 4/1993 | Edwards |
| 5,257,420 A | 11/1993 | Byrne, Jr. |
| 5,303,426 A | 4/1994 | Jones |
| 5,327,178 A | 7/1994 | McManigal |
| 5,339,467 A | 8/1994 | Brinkley |
| 5,357,585 A | 10/1994 | Kumar |
| 5,509,146 A | 4/1996 | Bryerton, Sr. |
| 5,528,774 A | 6/1996 | Sanders |
| 5,545,859 A | 8/1996 | Ullrich |
| 5,551,089 A | 9/1996 | Whidden |
| 5,551,090 A | 9/1996 | Thompson |
| D375,825 S | 11/1996 | Whidden |
| 5,617,589 A | 4/1997 | Lacore et al. |
| 5,625,903 A | 5/1997 | Schultz et al. |
| 5,673,438 A | 10/1997 | Lambert |
| 5,691,515 A | 11/1997 | Landis |
| D390,564 S | 2/1998 | Savona |
| 5,718,001 A | 2/1998 | Wright |
| 5,724,119 A | 3/1998 | Leight |
| 5,749,099 A | 5/1998 | Voorhees |
| 5,793,878 A | 8/1998 | Chang |
| 5,821,468 A | 10/1998 | Urella et al. |
| 5,835,609 A | 11/1998 | LeGette et al. |
| 5,860,166 A | 1/1999 | Ritts |
| 5,887,286 A | 3/1999 | Waldron |
| 5,898,945 A | 5/1999 | Weiser |
| 5,943,703 A | 8/1999 | Avila, Jr. |
| 5,953,434 A | 9/1999 | Boyden |
| 6,016,574 A | 1/2000 | Chen |
| 6,029,282 A | 2/2000 | Buschman |
| 6,055,672 A | 5/2000 | Natvig |
| 6,065,157 A | 5/2000 | Felman |
| 6,104,824 A | 8/2000 | Ito |

U.S. PATENT DOCUMENTS

| | | | |
|---|---|---|---|
| 6,148,446 | A | 11/2000 | Leight |
| 6,332,223 | B1 | 12/2001 | LeGette et al. |
| 6,377,697 | B1 | 4/2002 | Cheng |
| 6,499,146 | B2 | 12/2002 | Bavetta et al. |
| 6,502,247 | B2 | 1/2003 | LeGette et al. |
| 6,502,248 | B2 | 1/2003 | LeGette et al. |
| D473,539 | S | 4/2003 | O'Leary |
| 6,580,800 | B1 | 6/2003 | Yamasaki et al. |
| 6,735,784 | B2 | 5/2004 | Isom et al. |
| 6,744,901 | B2 | 6/2004 | Ito et al. |
| 6,880,174 | B2 | 4/2005 | Prokop |
| 6,888,950 | B2 | 5/2005 | Siskin et al. |
| 6,920,645 | B2 | 7/2005 | LeGette et al. |
| 6,978,483 | B2 | 12/2005 | Isom et al. |
| 7,024,013 | B1 | 4/2006 | Van Dam |
| 7,072,483 | B2 | 7/2006 | Lenhard-Backhaus |
| D541,482 | S | 4/2007 | Le Gette et al. |
| 7,210,173 | B2 | 5/2007 | Bavetta et |
| 7,212,645 | B2 | 5/2007 | Le Gette et al. |
| 7,222,373 | B2 | 5/2007 | Healy et al. |
| D545,001 | S | 6/2007 | Le Gette et al. |
| 2001/0017925 | A1 | 8/2001 | Ceravolo |
| 2003/0037366 | A1 | 2/2003 | Lindgren |
| 2005/0034216 | A1 | 2/2005 | LeGette et al. |
| 2005/0034217 | A1 | 2/2005 | Healy et al. |
| 2005/0034218 | A1 | 2/2005 | LeGette et al. |
| 2005/0036643 | A1 | 2/2005 | LeGette et al. |
| 2005/0241047 | A1 | 11/2005 | Bavetta et al. |
| 2005/0246815 | A1 | 11/2005 | LeGette et al. |
| 2006/0000006 | A1 | 1/2006 | Gellis et al. |
| 2006/0206983 | A1 | 9/2006 | Isom et al. |
| 2007/0107110 | A1 | 5/2007 | Le Gette et al. |
| 2008/0307562 | A1* | 12/2008 | Tipp ............................ 2/209 |
| 2008/0307563 | A1* | 12/2008 | Le Gette et al. ............... 2/209 |
| 2008/0307564 | A1* | 12/2008 | Le Gette et al. ............... 2/209 |
| 2008/0307565 | A1* | 12/2008 | Le Gette et al. ............... 2/209 |

FOREIGN PATENT DOCUMENTS

| | | | |
|---|---|---|---|
| CH | 294003 | | 1/1954 |
| CH | 662052 | | 9/1987 |
| CN | 2291138 | | 9/1998 |
| DE | 2516709 | A1 | 10/1976 |
| DE | 3231218 | A1 | 2/1984 |
| DE | 4422767 | A1 | 1/1996 |
| DE | 29800973 | U1 | 4/1998 |
| DE | 29812652 | U1 | 3/1999 |
| EP | 0745364 | | 8/2002 |
| FR | 1353524 | | 1/1963 |
| FR | 2536253 | A1 | 11/1982 |
| FR | 2538204 | A1 | 12/1982 |
| FR | 2532838 | A1 | 9/1983 |
| GB | 1327614 | | 8/1973 |
| GB | 2062478 | | 5/1981 |
| GB | 2320885 | | 8/1998 |
| GB | 2339642 | | 2/2000 |
| JP | 4719024 | | 11/1972 |
| JP | 4875626 | | 9/1973 |
| JP | 53143627 | | 11/1978 |
| JP | 56-152479 | | 11/1981 |
| JP | 5711884 | | 1/1982 |
| JP | 6029141 | | 2/1982 |
| JP | 57205216 | | 12/1982 |
| JP | 5815618 | | 1/1983 |
| JP | 58-104076 | | 7/1983 |
| JP | 58138484 | | 9/1983 |
| JP | 59129815 | | 8/1984 |
| JP | 60244188 | | 12/1985 |
| JP | 61-42186 | | 3/1986 |
| JP | 623526 | | 1/1987 |
| JP | 6221016 | | 2/1987 |
| JP | 6320232 | | 6/1988 |
| JP | 1125319 | | 8/1989 |
| JP | 641720 | | 6/1994 |
| JP | 6351090 | | 12/1994 |
| JP | 1079994 | | 3/1998 |
| JP | 10085251 | | 7/1998 |
| JP | 11229223 | | 8/1999 |
| JP | 10257581 | | 8/2000 |
| JP | 200211036 | | 1/2002 |
| KR | 200226271 | | 3/2001 |
| KR | 200314976 | | 6/2003 |
| KR | 300336877 | | 11/2003 |
| KR | 20357405 | | 7/2004 |
| KR | 20357406 | | 7/2004 |
| WO | 9217079 | A1 | 10/1992 |
| WO | 9409734 | A1 | 5/1994 |
| WO | 9748296 | A1 | 12/1997 |
| WO | 9807062 | A1 | 2/1998 |
| WO | 9831314 | A1 | 7/1998 |
| WO | 0176402 | A1 | 10/2001 |
| WO | 02083044 | A1 | 10/2002 |
| WO | 03086124 | A1 | 10/2003 |

OTHER PUBLICATIONS 1999-2000 Catalog "Accessory Goods"—Nitty Company, Ltd. 4 pgs.
Chicago Tribune article entitled "Winter From Head to Toe Lend an Ear to the Tale of This Intrepid Inventor," by Sid Moody, Feb. 16, 1988, 4 pgs.
"History of the United States Patent Office—The Patent Office Pony—A History of the Early Patent Office," by Kenneth W. Dobyns, 1994, [Introductory Material—3 pgs; Chapter 29—4 pgs; and Sources and Annotations—40 pgs.].
2003 Catalog, "Join the Polar Fusion Revolution; Revolutionary Ear Warmers," Polar Fusion LLC.—2 pgs.
Nitty Company Ltd. Winter '89-'90 catalog, 6 pages.
Nitty Company Ltd., Winter '90-'91 catalog, 4 pages.
"Hearmuff: Fleece headwear with internal stereo headphones" from http://www.hearmuff.com/index.htm, 2003, 1 pg.
"Hearmuffs" from http://www.hearmuff.com/goods.htm, 2003, 2 pgs.
"Hearmuffs" from http://www.hearmuff.com/about.htm, 2003, 3 pgs.

* cited by examiner

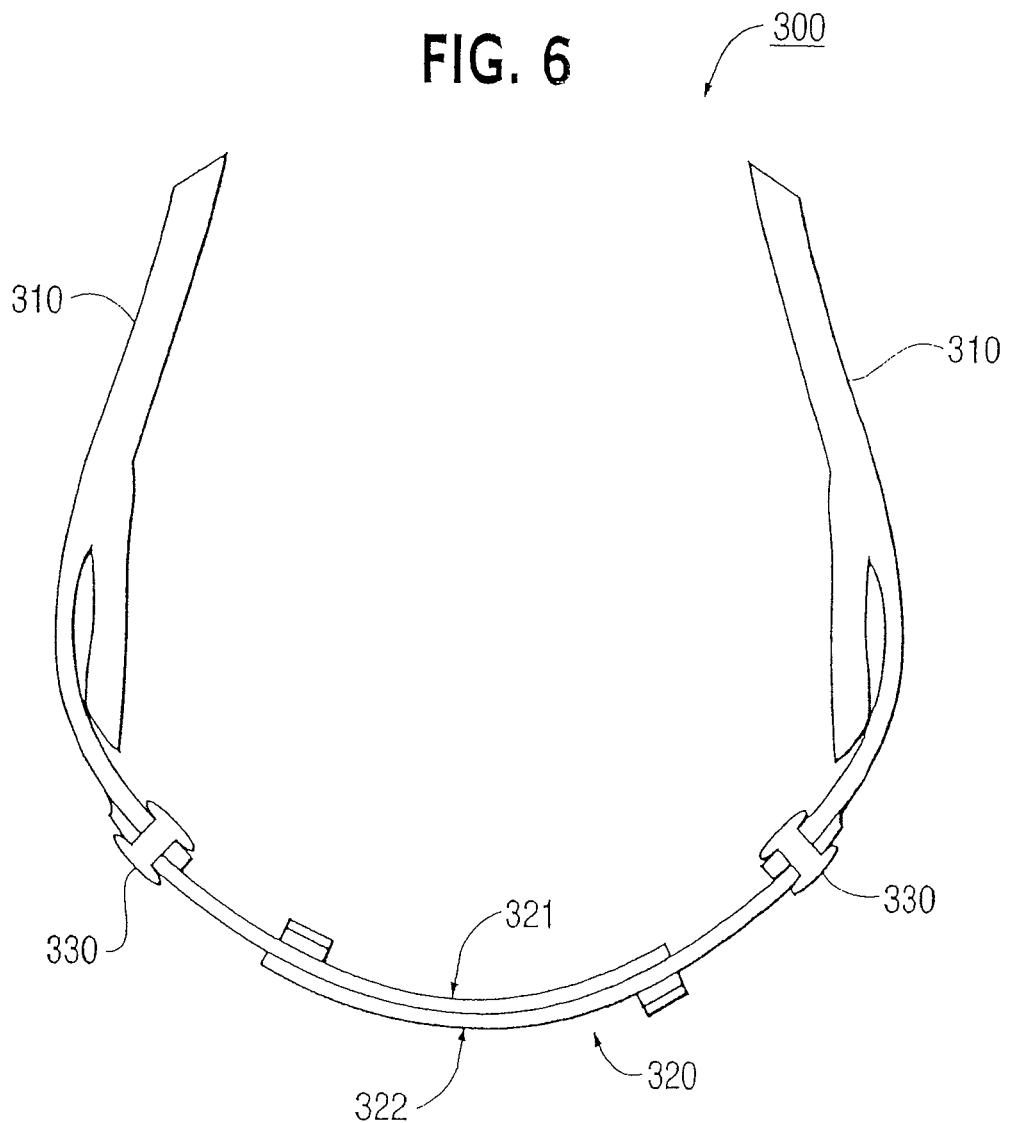

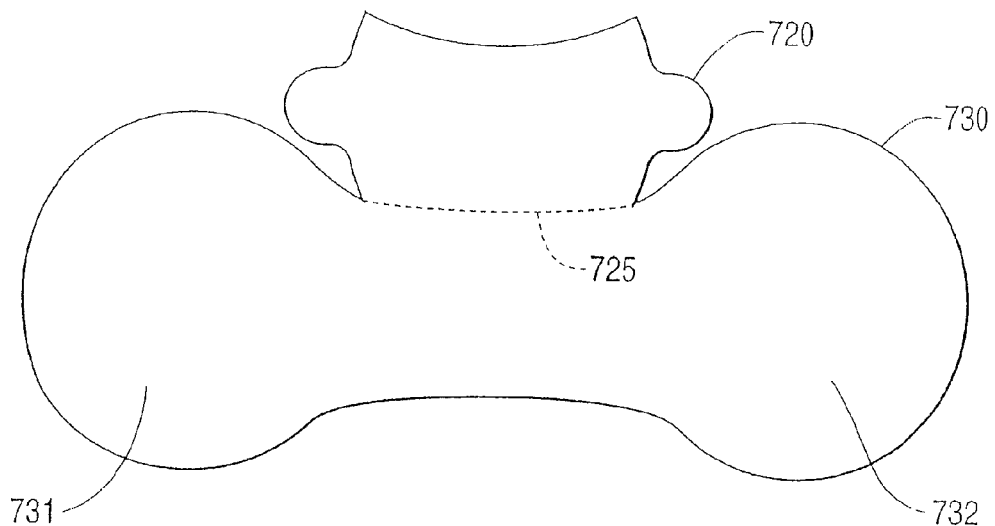
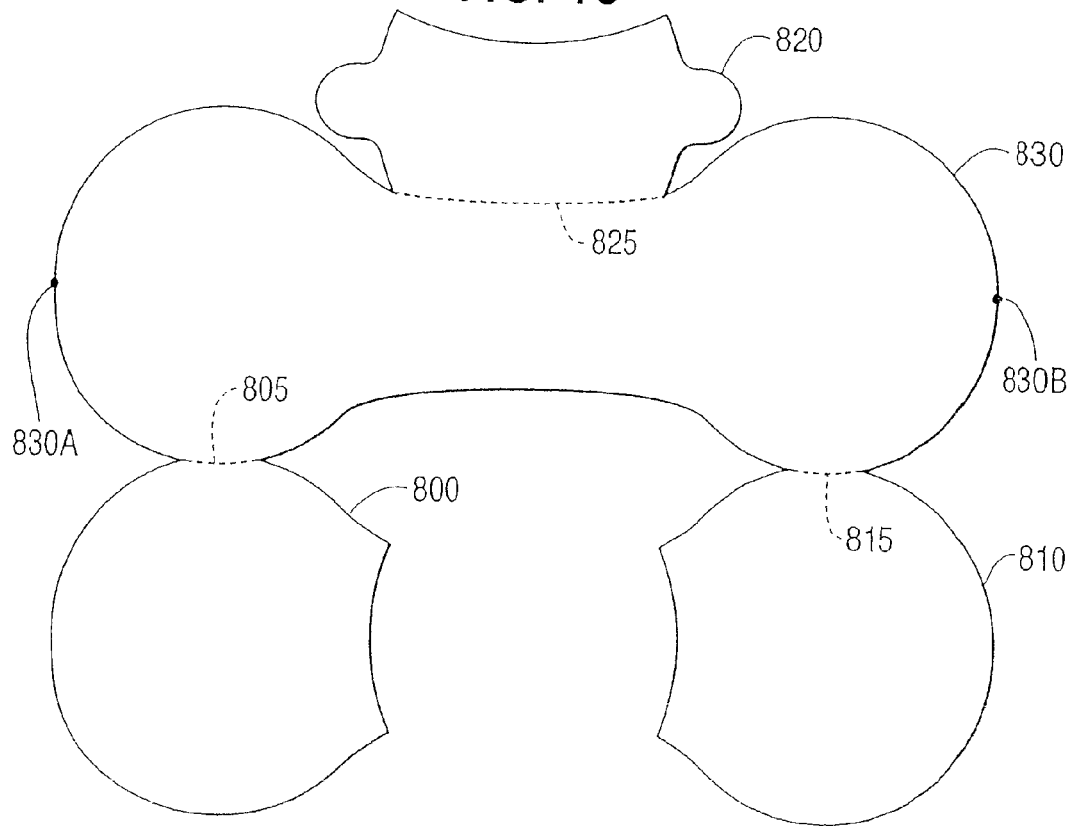

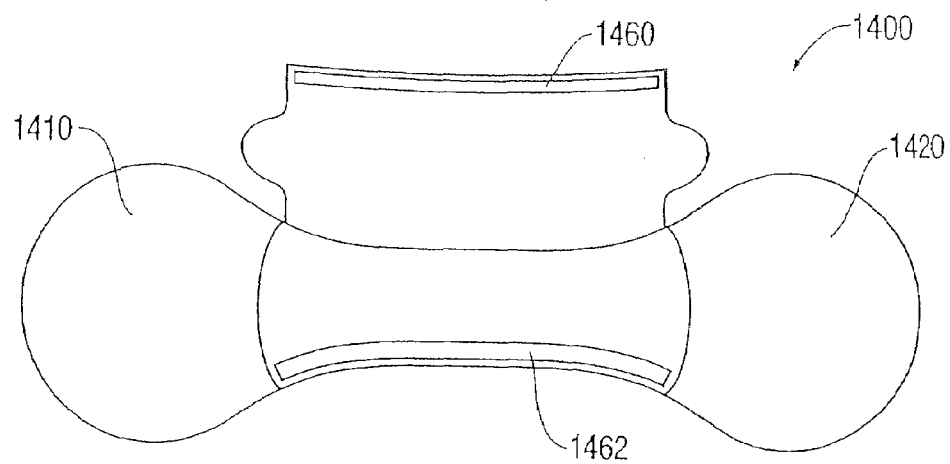
FIG. 24
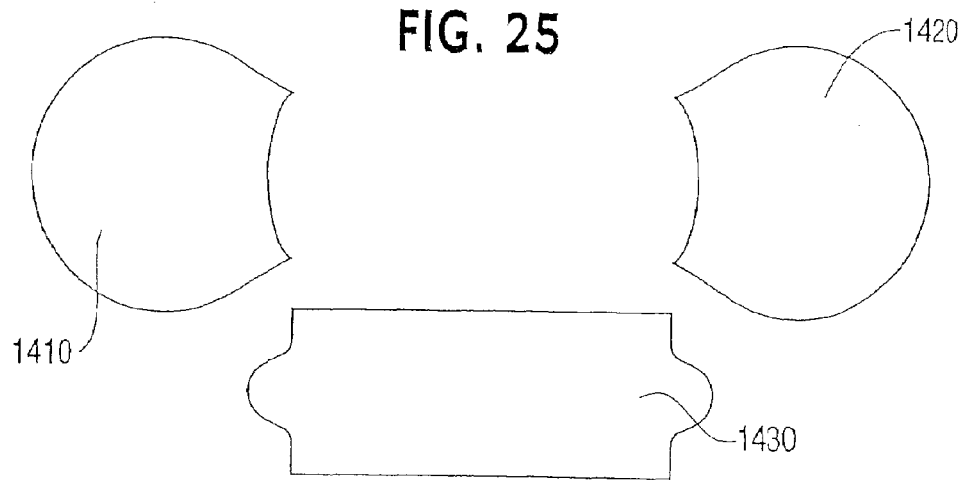
FIG. 25
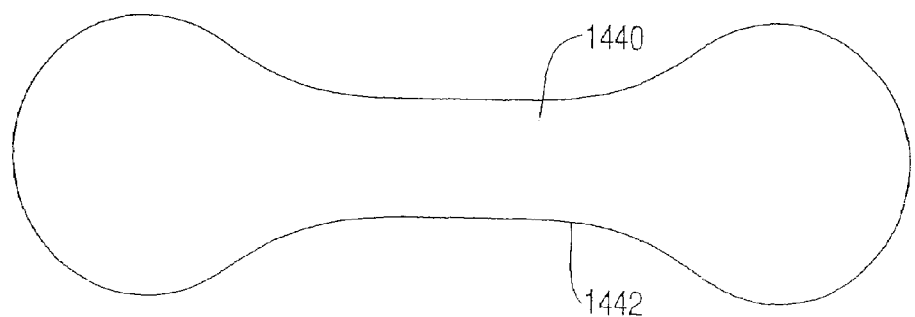

FIG. 28
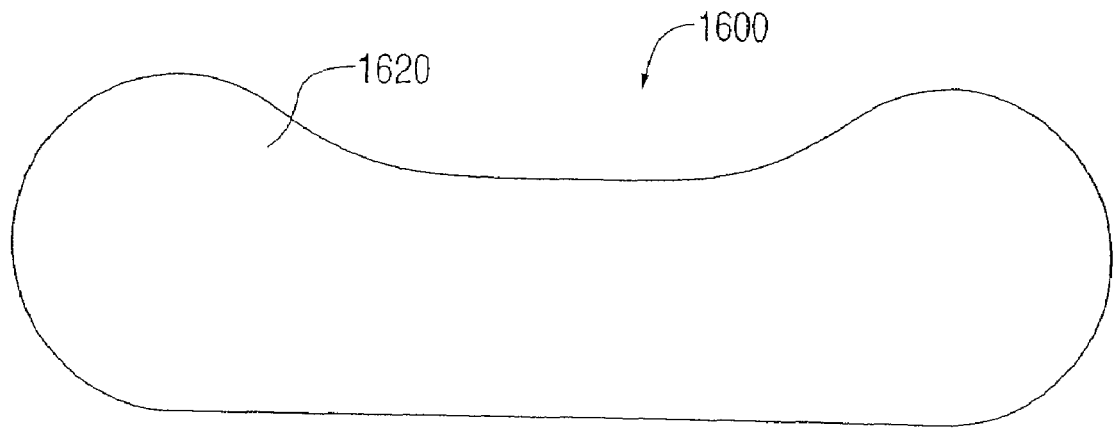
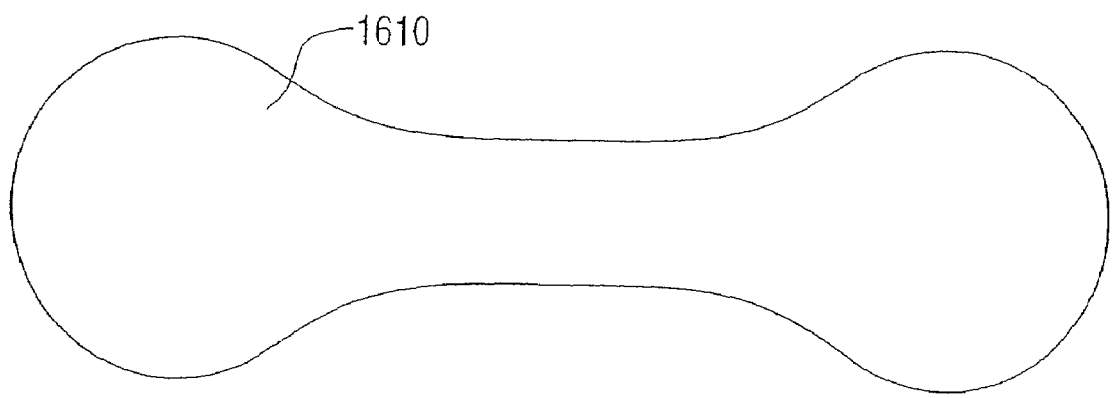

US 7,617,543 B2

APPARATUS AND METHOD FOR MAKING AN EAR WARMER AND AN EAR WARMER FRAME

CROSS-REFERENCE TO RELATED APPLICATIONS

This application is a continuation application of U.S. patent application Ser. No. 11/619,424, entitled "Apparatus and Method for Making an Ear Warmer and an Ear Warmer Frame," filed Jan. 3, 2007, which is a continuation application of U.S. patent application Ser. No. 11/108,615, entitled "Apparatus and Method for Making an Ear Warmer and an Ear Warmer Frame," filed Apr. 18, 2005, which is a continuation of U.S. patent application Ser. No. 10/335,930, entitled "Apparatus and Method for Making an Ear Warmer and an Ear Warmer Frame," filed Jan. 3, 2003, now U.S. Pat. No. 6,920,645 B2, issued Jul. 26, 2005, which is a continuation of U.S. patent application Ser. No. 09/986,103, entitled "Apparatus and Method for Making an Ear Warmer and an Ear Warmer Frame," filed Nov. 7, 2001, now U.S. Pat. No. 6,502,248 B2, issued Jan. 7, 2003, which is a continuation of PCT Application Serial No. PCT/US01/11041, entitled "Apparatus and Method for Making an Ear Warmer and an Ear Warmer Frame," filed Apr. 5, 2001, which is a continuation-in-part of U.S. patent application Ser. No. 09/521,241, entitled "Apparatus and Method for Making an Ear Warmer Having Interior Seams," filed Apr. 5, 2000, now U.S. Pat. No. 6,332,223 B1, issued Dec. 25, 2001. The entire disclosure of each of the above-identified applications is incorporated by reference herein in its entirety. This application is related to U.S. patent application Ser. No. 09/978,591, entitled "Apparatus and Method for Making an Ear Warmer Having Interior Seams," filed Oct. 18, 2001, now U.S. Pat. No. 6,502,247 B2, issued Jan. 7, 2003, the entire disclosure of which is incorporated by reference in its entirety.

BACKGROUND

The present invention relates to an ear warmer device. More specifically, the present invention relates to an apparatus and a method for making an ear warmer having interior seams and an ear warmer frame.

SUMMARY OF THE INVENTION

An ear warmer comprises a set of membranes and a frame. The set of membranes collectively defines an outer perimeter. The set of membranes is attached along a portion of the outer perimeter or the entire outer perimeter to define an attachment portion. The attachment portion is entirely disposed within an interior of the set of membranes. The frame is disposed within the interior of the set of membranes.

BRIEF DESCRIPTION OF THE DRAWINGS

FIG. 6 illustrates a top view of a frame that can be disposed within an ear warmer shell to form an ear warmer, according to an embodiment of the present invention.

FIG. 12 illustrates a set of membranes for use in constructing an ear warmer, according to another embodiment of the present invention.

FIG. 13 illustrates a membrane for use in constructing an ear warmer, according to yet another embodiment of the present invention.

FIGS. 24-25 illustrate a set of membranes for use in constructing an ear warmer, according to another embodiment of the invention.

FIGS. 27-29 illustrate a set of membranes for use in constructing an ear warmer, according to another embodiment of the invention.

DETAILED DESCRIPTION

An ear warmer comprises a set of membranes and a frame. The set of membranes collectively defines an outer perimeter. The set of membranes is attached along a portion of the outer perimeter or the entire outer perimeter to define an attachment portion. The attachment portion is entirely disposed within an interior of the set of membranes. The frame is disposed within the interior of the set of membranes.

The term "attachment portion" is defined herein as a portion of the set of membranes between the attachment and the outer edge of the membranes. For example, the ear warmer membranes can be sewn together along their collective perimeter or a portion of that collective perimeter and then turned inside out. In such a case, the sewn seam as well as the extra portion of the membranes between the sewn seam and the outer edge of the membranes are inside the ear warmer; the frame can be inserted into the interior of the membranes. Alternatively, the ear warmer membranes can be bound along their collective perimeter or a portion of that collective perimeter.

As described in greater detail below, the set of membranes may be sewn, bound, or sewn and turned inside out. The set of membranes can be coupled together using a combination of sewing, binding, and sewing and then turning inside out.

Figure 1:
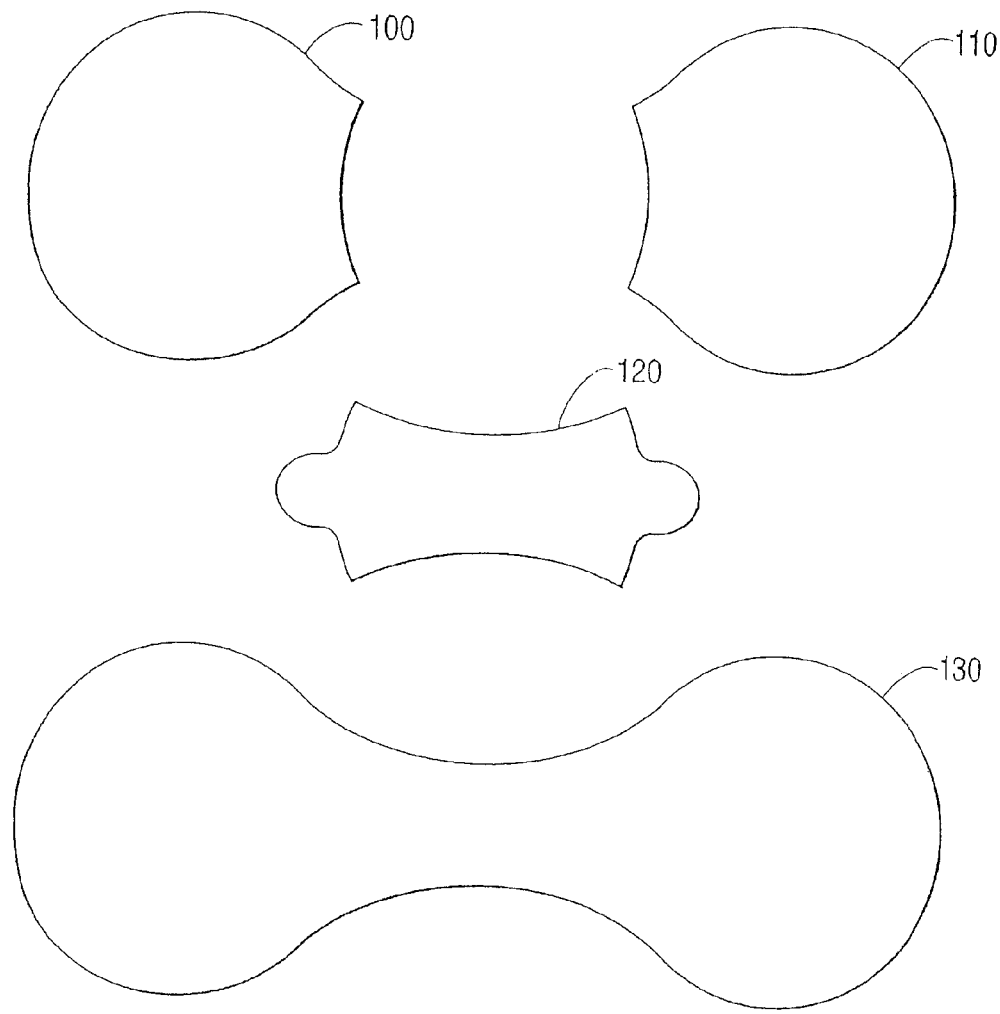
FIG. 1 illustrates a set of membranes for use in constructing an ear warmer, according to an embodiment of the present invention.

FIG. 1 illustrates a set of membranes for use in constructing an ear warmer, according to an embodiment of the present invention. As shown in FIG. 1, an ear warmer can be constructed from first ear membrane 100, second ear membrane 110, middle membrane 120 and outer membrane 130. Membranes 100 through 130 can be made of various types of material appropriate for providing warmth while also being comfortable on the wearer's skin. For example, membranes 100 through 130 can be made of such materials as fleece, wool, cotton, foam and/or neoprene.

Figure 2:
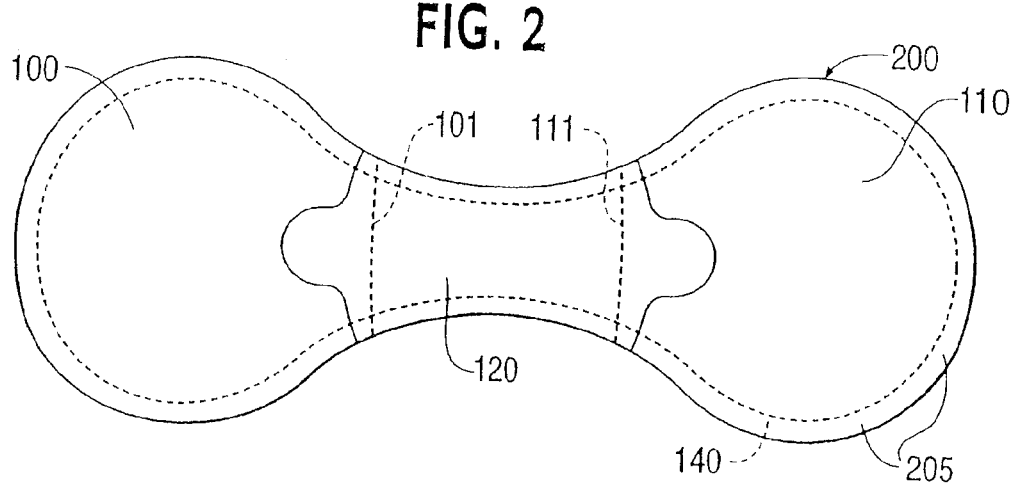
FIG. 2 illustrates an arrangement of an ear warmer shell during an interim step in an assembly process, according to an embodiment of the present invention.

FIG. 2 illustrates an arrangement of an ear warmer shell during an interim step in an assembly process, according to an embodiment of the present invention. Ear warmer shell 200 includes an arrangement of membranes 100 through 130 where they have been attached together via attachment 140 along the perimeter of the collection of membranes (i.e., along the perimeter of ear warmer 200). Attachment portion 205 is the portion of membranes 100 through 130 between and including attachment 140 and the edge of membranes 100 through 130. For example, when ear warmer membranes 100 through 130 are attached by sewing the membranes together along a portion of their collective perimeter, attachment portion 205 is the extra portion of the membranes between the sewn seam and the outer edge of the membranes.

More specifically, ear warmer shell 200 can be constructed by first disposing first ear membrane 100 and second ear membrane 110 on top of outer membrane 130. Middle membrane 120 can then be placed on top of the set of outer membrane 130, ear membrane 100 and ear membrane 110 in the arrangement shown in FIG. 2. Ear membranes 100 and 110, and middle membrane 120 are on top of each other and outer membrane 130 in the sense that they are ordered in a particular way; the particular orientation of the collection of membranes as shown in the figures herein are not important. The arrangement of membranes 100 through 130 can then be attached along the perimeter of ear warmer 200 via attachment 140. A portion of the perimeter of ear membrane 100 is not attached to outer membrane 130; this unattached perimeter portion is labeled as 101. Similarly, a portion of the perimeter of ear membrane 110 is not attached to outer membrane 130; this unattached perimeter portion is labeled as 111.

As discussed above, a variety of couplings can be used to secure the membranes together. For example, in one embodiment, ear membranes 100 and 110 and middle membrane 120 can be bound to outer membrane 130. In another embodiment, ear membranes 100 and 110 can be sewn to the outer membrane 130 and turned inside out and the middle membrane 120 can be bound to the outer membrane 130. In an alternative embodiment, the middle membrane 120 can be sewn to the outer membrane 130 and turned inside out and the ear membranes 100 and 110 can be bound to outer membrane 130. As apparent, any combination of sewn, bound, and sewn and inside out couplings can be used.

Figure 3:
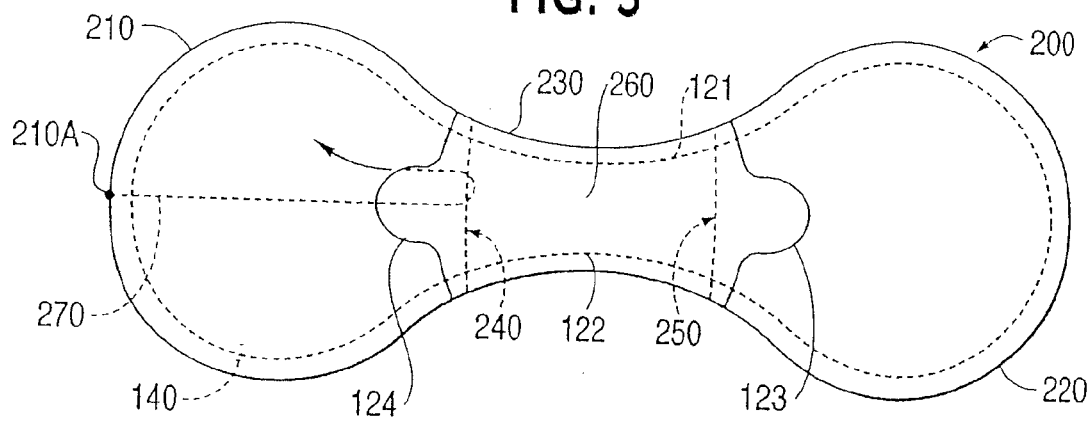
FIGS. 3, 4 and 5 illustrate top views of the ear warmer shell of FIG. 2 at different steps in a method for assembling an ear warmer, according to an embodiment of the present invention.

FIGS. 2, 3, 4 and 5 illustrate ear warmer shell 200 at different steps in a method for assembling an ear warmer, according to an embodiment of the present invention. As shown in FIG. 3, ear warmer shell 200 includes a first ear portion 210, a second ear portion 220 and a middle portion 230. First ear portion 210 includes opening 240 that is formed by the perimeter portion 101 of ear membrane 100. Similarly, second ear portion 220 includes opening 250 that is formed by the perimeter portion 111 of ear membrane 110.

Channel 260 is formed by middle portion 120 and the portion of outer membrane 130 disposed with middle membrane 120. More specifically, middle membrane 120 is attached along two portions 121 and 122 of its perimeter to outer membrane 130 while the two remaining portions 123 and 124 of the perimeter of middle membrane 120 are not attached to outer membrane 130. These unattached perimeter portions of middle membrane 120 generally correspond to openings 240 and 250, thus channel 260 is formed between the attached perimeter portions of middle membrane 120 from opening 240 to opening 250.

Figure 4:
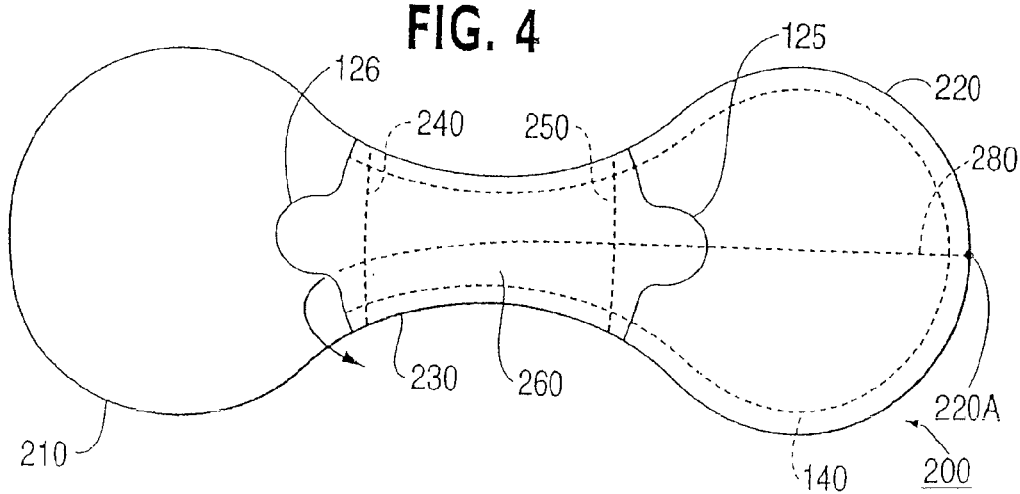

As shown in FIG. 3, ear portion 210 can be turned inside out through opening 240. More specifically, line 270 shows the direction in which ear portion 210 should be moved to turn it inside out. The outer edge 210A of ear portion 210 is moved through opening 240 so that ear portion 210 is turned inside out. In otherwords, an interior formed by ear membrane 100 and outer membrane 130 is turned outward by moving the end 210A of ear portion 210 along line 270 through opening 240 and then completely turned outward as shown in FIG. 4. In this manlier, attachment 140 (e.g., an externally sewn seam) along the perimeter of ear portion 210 is turned inward so that a portion of the attachment 140 is located within a newly defined interior portion of ear portion 210. Consequently, this portion of attachment 130 is not visible from the outside of ear warmer shell 200, and rather is internal to ear warmer shell 200.

FIG. 4 illustrates another step for assembling an ear warmer according to an embodiment of the present invention. The outer edge 220A of ear portion 220 is turned inside out along line 280 so that the outer edge of ear portion 220 is moved through channel 260 and through opening 240. Once ear portion 220 is partially turned inside out within channel 260, it can be further moved along motion line 280 through the use of an additional device such as a dowel so that ear portion 220 can completely transit the channel 260 and be moved through opening 240.

Note that as ear portion 220 is turned inside out as described above in reference to FIG. 4, the middle portion 230 is also turned inside out. In other words, as the outer edge of ear portion 220 is turned inside out, the middle portion 230 is moved through its channel 260 and through opening 240. Consequently, middle portion 230 is turned inside out so that the exterior sides of middle portion 230 as shown in FIGS. 2 and 3 are now interior to ear warmer shell 200 as shown in FIG. 4.

Figure 5:
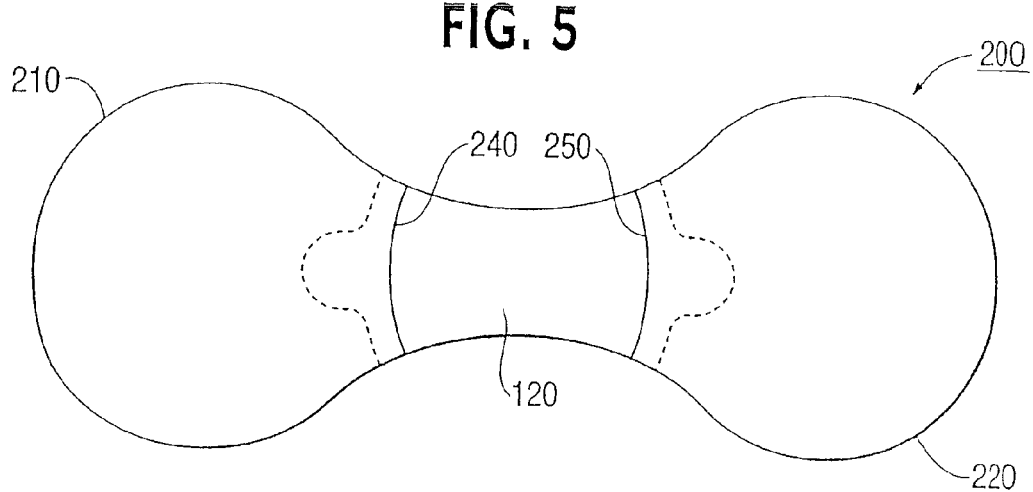

The unattached portions 125 and 126 of middle membrane 120 can then be placed through the respective openings 240 and 250 so that the ends of middle membrane 120 (shown, for example, as having tabs in FIGS. 3-5) are not visible from the outside but rather are disposed within the interior formed by ear membrane 100 and outer membrane 130 on one side of ear warmer shell 200 and formed by ear membrane 110 and outer membrane 130 are on the other end of ear warmer shell 200. Thus, as shown in FIG. 5, attachment 140 (e.g., the sewn seams) that was externally visible as the membranes were initially attached along the outer perimeter of ear warmer shell 200 (as illustrated, for example, in FIG. 2) are now all internal to ear warmer shell 200 and not visible from the exterior as shown in FIG. 5. In such a case, ear warmer shell 200 has a different appearance from that disclosed in U.S. Pat.

No. 5,835,609 while yet being an aesthetically pleasing appearance and also obviating the need for binding over an external seam.

FIG. 6 illustrates a top view of a flame that can be disposed within an ear warmer shell to form an ear warmer, according to an embodiment of the present invention. Frame 300 includes a first frame member 310, a second frame member 310 and a third frame member 320. Frame member 320 can be, for example, a slidably adjustable band having an inner curved side 321 and an outer curved side 322. U.S. Pat. No. 5,835,609 discloses an example of frame 300 including frame members 310 and 320 and is incorporated herein by reference (see, e.g., FIGS. 28-38 and the associated written description in U.S. Pat. No. 5,835,609). Connection 15 device 330 (such as a rivet) can attach frame members 310 to frame member 230.

Figure 7:
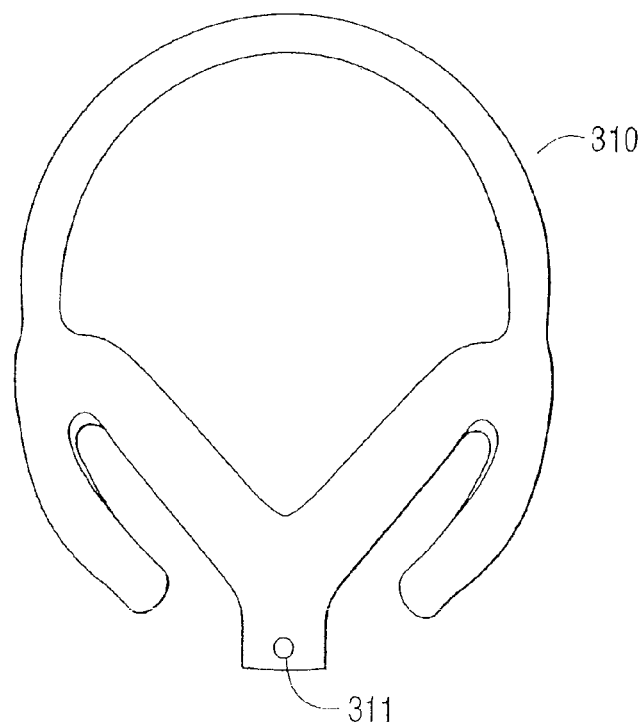
FIG. 7 illustrates a frame member of a frame to be inserted into an ear warmer shell, according to an embodiment of the present invention.

FIG. 7 illustrates a frame member of a frame to be inserted into an ear warmer shell, according to an embodiment of the present invention. More specifically, frame member 310 may have any shape that is conducive to being comfortably placed against a user's ear. For example, in one embodiment, frame member 310 has a frusto-conical shape. In another embodiment, frame member 310 has a frusto-hemispherical shape.

Frame member 310 can include a connection portion 311. In the embodiment shown in FIG. 7, the connection portion 311 can include a rivet hole that aligns with a similar rivet hole in third frame member 320 (shown in FIG. 6); connection device 330 can then attach frame members 310 to frame member 320 via their respective connection portions 311. Alternatively, a connection portion of a frame member (similar in function to connection portion 311 and connection device 330 of frame member 300) can be an integral snap-fit connector that complementarily fits with an associated portion on a band-like frame member (similar to frame member 320).

The unattached frame members of frame 300 can be inserted into ear warmer shell 200 and then attached together by the following steps. First, a frame member 310 can be inserted into ear portion 210 through opening 240. Similarly, a second frame member 310 can be inserted in ear portion 220 through opening 250. Of course, frame members 310 can be oriented with respect to the membranes (and the wearer's head) appropriately; for example, outer membrane 130 can be positioned along the rear, outward facing (i.e., not adjacent to the wearer's head) with respect to the ear warmer. In such a case, the frame members 310 should be inserted into the respective interiors of ear portions 210 and 220 such that the relative base of the frame members 310 is disposed towards the wearer's ears (i.e., the curvature of frame member 310 is similar to the wearer's head). Similarly, middle membrane 120 should be disposed inwardly adjacent to the wearer's head when the ear warmer is completely assembled and worn by the wearer.

In the next step in the method for inserting the frame, frame member 320 can be inserted into channel 260 through either opening 240 or 250. Again, frame member 320 should be disposed within channel 260 so that the curvature of frame member 320 is similar to the curvature of the user's head.

The ends of frame members 310 can be connected to the respective ends of frame member 320. Once frame members 310 and frame member 320 are appropriately positioned within the interior of ear warmer shell 200, connection portion 311 of frame member 310 can be disposed through opening 240 along with the corresponding end of frame member 320 so that frame member 310 and frame member 320 can be attached by connection devices 330. The other end of frame member 320 can likewise be attached to the other frame member 310.

Once the three frame members are attached to form frame 300, the ear warmer shell 200 can be arranged so that frame 300 is completely disposed within the interior ear warmer shell 200 and is not visible from the exterior. This can be accomplished, for example, by disposing the respective connected ends of frame members 310 and frame member 320 back into the interior ear warmer shell 200. The tab-like ends of middle membrane 120 can then be reinserted into openings 240 and 250 so that the assembling of the ear warmer including its ear warmer shell 200 and frame 300 is complete.

Figure 8:
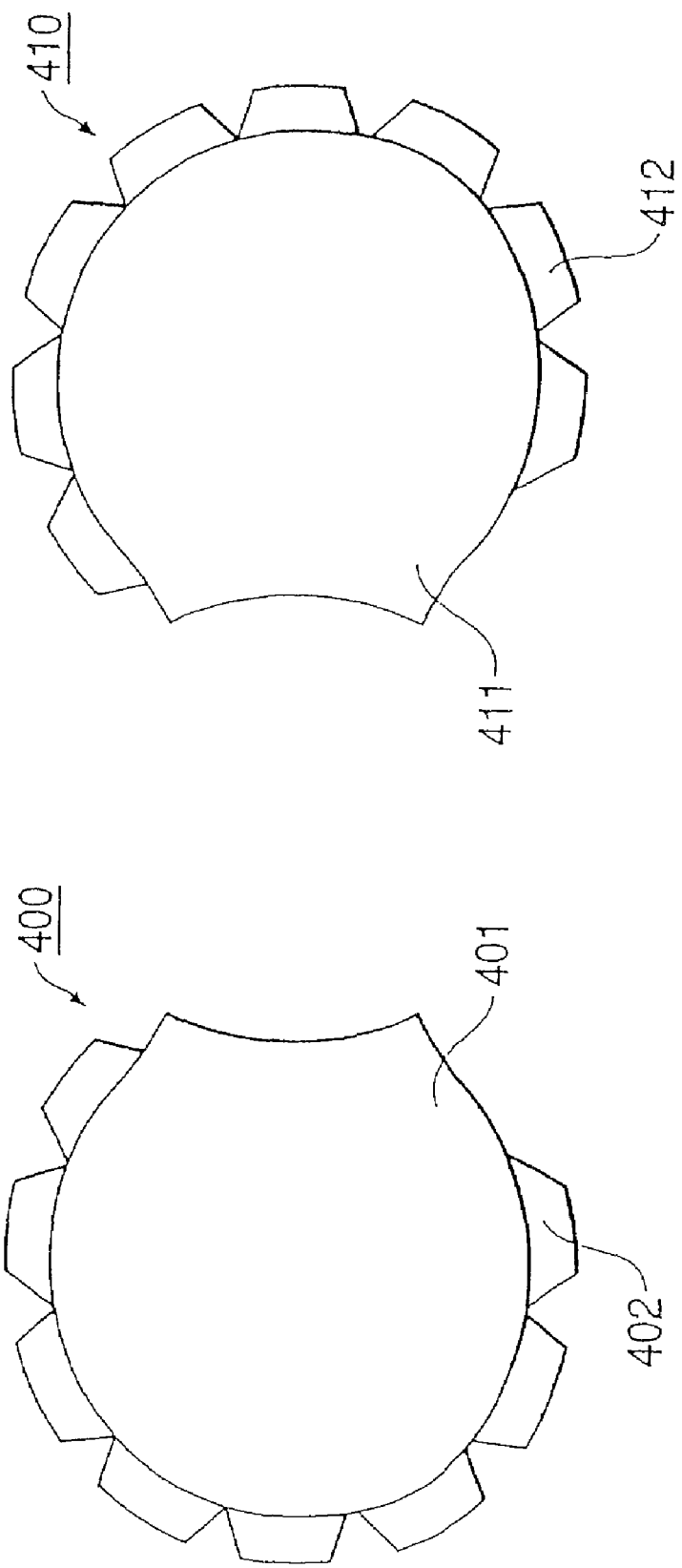
FIG. 8 illustrates ear membranes according to an alternative embodiment of the present invention.

FIG. 8 illustrates ear membranes according to an alternative embodiment of the present invention. Ear membrane 400, as shown in FIG. 8, includes central portion 401 and extended portions 402. Likewise, ear membrane 410 includes central portion 411 and extended portions 412. Note, although only one extended portion is labeled as 402 for ear membrane 400 and, similarly, only one extended portion is labeled 412 for ear membrane 410 in FIG. 8, this notation in FIG. 8 is merely for convenience and would apply to one or more extended portions as appropriate. In an alternative embodiment, each ear membrane may have only one extended portion.

Ear membranes 400 and 410 can be substituted for ear membranes 100 and 110 as described in the apparatus and method described above in reference to FIGS. 1-7. In such an embodiment, the perimeter seams discussed in conjunction with FIG. 2 above would be formed along the partial perimeter of central portion 401 and 411 of ear membranes 400 and 410, respectively. In other words, extended portions 402 and 412 of ear membranes 400 and 410, respectively, are disposed outside of the collective perimeter for the ear warmer shell.

When the ear warmer shell is then turned inside out, for example as discussed above in reference to FIGS. 3-5, the extended portions 402 and 412 of ear membranes 400 and 410, respectively, are located within the interior of the ear warmer shell and form an additional layer of fabric. For example, FIG. 9 illustrates the extended portions of the ear membranes forming an added layer of fabric within the interior of the ear warmer shell.

Figure 9:
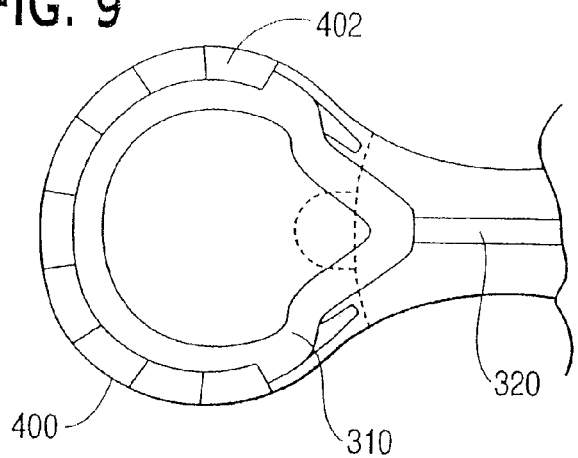
FIG. 9 illustrates a top view of a left portion of an ear warmer, according to an embodiment of the present invention.

More specifically, FIG. 9 illustrates a left portion of an ear warmer, according to an embodiment of the present invention. As illustrated in FIG. 9, the ear portion of the left side of FIG. 9 has the extended portions 402 (shown in phantom) of ear membrane 400 being disposed within the interior of an ear warmer shell such that they form a nearly continuous piece of additional fabric. In such a case, the frame member 310 (shown in phantom) when inserted into an interior of an ear warmer shell can be disposed between extended portions 402 and outer membrane 130. In such an embodiment, extended portions 402 provide an extra layer of cushioning fabric that is disposed between frame member 310 and the wearer's head. In other words, in such an embodiment, extended portions 402 and 412 in addition to central portions 401 and 411 of ear membranes 400 and 410, respectively, are disposed between the wearer and the frame member 310. Extended portions 402 and 412 also prevent the ear membranes from pulling around the frame members 310 and keep the perimeter of the ear membranes at the edge of the frame members 310.

Figure 10:
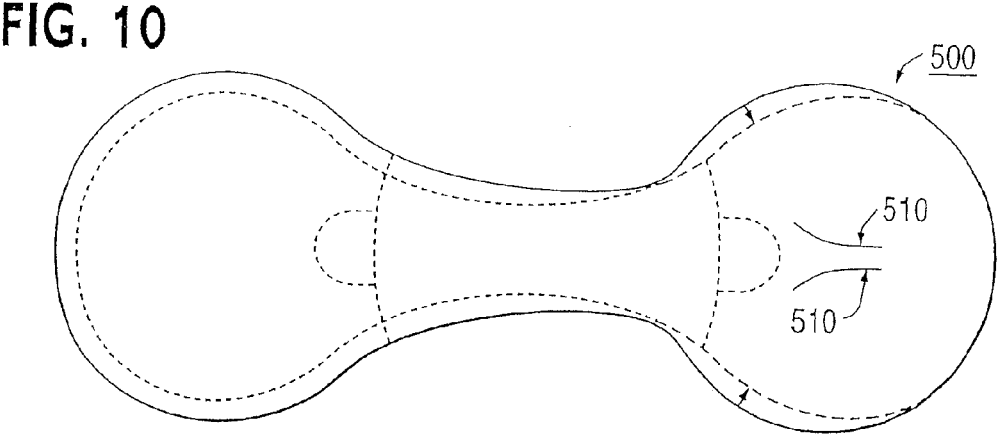
FIG. 10 illustrates a top view of an ear warmer shell, according to another embodiment of the present invention.

FIG. 10 illustrates an ear warmer shell according to another embodiment of the present invention. In such an embodiment of ear warmer shell 500, the ear membranes can have a size slightly smaller than the corresponding portions of the outer membrane. The extra material of the outer membrane portions corresponding to the ear membranes allows the frame (once inserted into the ear warmer shell) to better fit within the ear warmer shell 500. In other words, because the frame to be inserted into the ear warmer shell is curved, the outer curved side (e.g., outer curved side 322 as shown in FIG. 6) of the frame is a greater distance than the inner curved side (e.g., inner curved side 321 as shown in FIG. 6) of the frame. Thus, the extra material of the outer membrane allows the ear warmer shell 500 to better fit around the curved shape of the frame.

The method to construct ear warmer shell 500 is similar to that described above in reference to FIGS. 2-5. Before attaching (e.g., by sewing) the collective perimeter of the membranes, the portion of the outer membrane corresponding to an ear membrane can be pinched inwardly along lines 510 to gather the perimeter of the outer membrane to more closely match the corresponding perimeter of the ear membrane. For example, the portion of the outer membrane corresponding to an ear membrane can be pinched and held inwardly with a clip (such as a binder clip), then the collective perimeter or a portion of the collective perimeter of the membranes can be attached. Thus, collective perimeter of the membranes are aligned when the membranes are being attached while allowing the outer membrane to have extra material so that the frame can better fit within the ear warmer shell 500.

Figure 11:
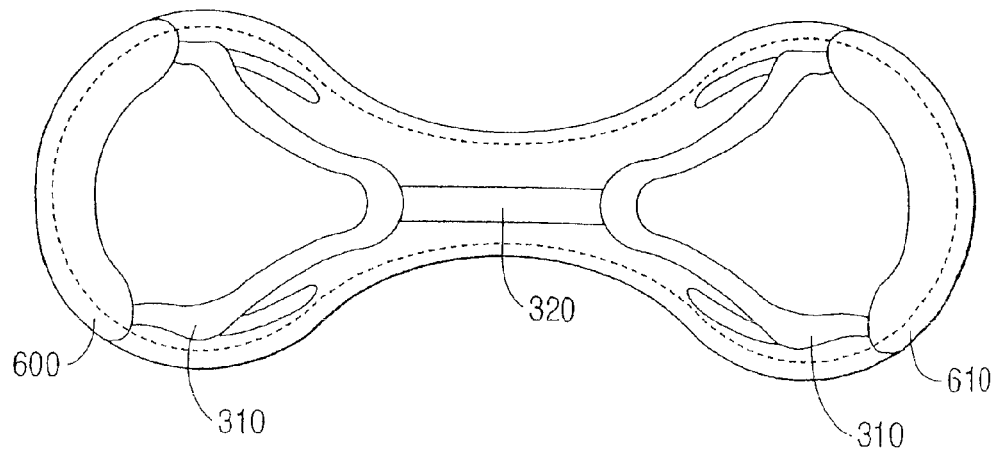
FIG. 11 illustrates internal components of an ear warmer shell, according to yet another embodiment of the present invention.

FIG. 11 illustrates internal components of an ear warmer shell, according to yet another embodiment of the present invention. For purposes of clarity, a covering portion of the ear warmer has been removed to show the internal components of the ear warmer. In this embodiment of an ear warmer shell, pocket membranes 600 and 610 (shown in phantom) are included. In such an embodiment, these additional and separate membranes, i.e., pocket membranes 600 and 610, can be attached (shown in phantom) along the respective portions of the collective perimeter of the ear warmer shell. In other words, pocket membranes 600 and 610 are attached to respective portions of outer membrane 130 and each form a respective pocket into which a frame member 310 can be inserted.

The pocket membranes 600 and 610, provide additional cushioning between frame members 310 (shown in phantom) and the head of the user. Pocket membranes 600 and 610 also prevent the membranes from pulling around the frame members 310 and keep the perimeter of the membranes at the edge of the frame members 310. In one embodiment, pocket membranes 600 and 610 can be attached on top of the respective ear membranes. Thus, when the ear warmer shell is turned inside out (as described above, for example, in reference to FIGS. 3-5), pocket membranes 600 and 610 are appropriately positioned within the ear warmer shell. Pocket membranes 600 and 610 may be any material that can be coupled to the outer membrane, such as plastic or fabric.

FIG. 12 illustrates a set of membranes for use in constructing an ear warmer, according to another embodiment of the present invention. Similar to the outer membrane 130 and the middle membrane 120 shown in FIG. 1, FIG. 12 illustrates a membrane having an outer portion 730 and a middle portion 720. The membranes can be arranged as follows. First, the ear membranes (e.g., ear membranes 100 and 110) can be placed on the corresponding portions of outer portion 730, i.e., portions 731 and 732 of outer portion 730. Middle portion 720 can then be folded on to outer portion 730 along the line 725. The collective perimeter can then be sewn, bound, or sewn and the membranes can be turned inside out as described above in reference to FIGS. 3-5.

FIG. 13 illustrates a membrane for use in constructing an ear warmer, according to yet another embodiment of the present invention. Similar to ear membrane 100, ear membrane 110, middle membrane 120 and outer membrane 130 shown in FIG. 1, FIG. 13 illustrates a membrane having ear portion 800, ear portion 810, middle portion 820 and outer portion 830. The membrane portions can be arranged as follows. First, the ear portions 800 and 810 can be folded on to the corresponding portions of outer portion 830 along lines 805 and 815, respectively. Middle portion 820 can then be folded on to outer portion 830 along the line 825. The collective perimeter can then be sewn, bound, or sewn and the membranes can be turned inside out as described above in reference to FIGS. 3-5.

Rather than the separate membranes shown in FIG. 1 variations to FIGS. 12 and 13 are possible where certain membranes are integrally formed together and folded over. For example, in another embodiment, only one ear membrane is integrally formed with the outer membrane, only two ear membranes are integrally formed with the outer membrane, or only one ear membrane and the middle membrane are integrally formed with the outer membrane.

In another alternative embodiment, the membranes can be integrally formed together at various locations (e.g., discontinuous locations) rather than along the entire fold (such as line 725 shown in FIG. 12). In yet another embodiment, the membranes can be integrally formed at various locations relative to the outer portion of the membrane. For example, rather than the ear portions being integrally formed at the lower location of the outer portion (as shown in FIG. 13), the ear portions can be integrally formed with the outer portion at other locations, such as the side locations 830A and 830B of the outer portion. The various locations that are possible are those where the portions of the membrane (i.e., the middle portion, and/or the ear portions) fold on to the outer portion of the membrane to appropriately form the ear warmer shell.

Figure 14:
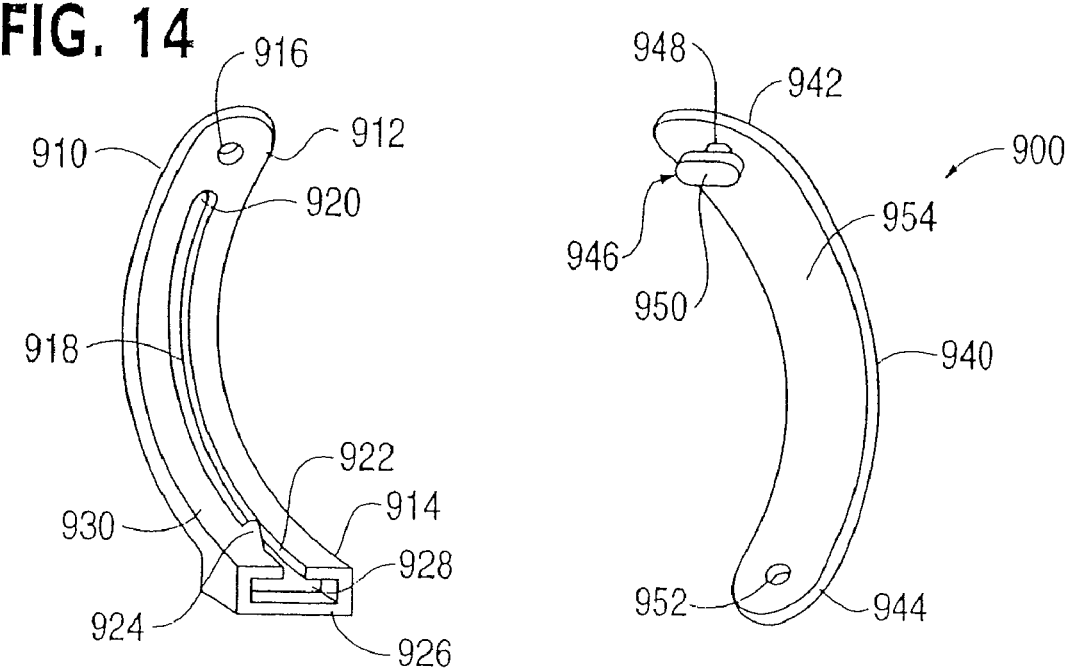
FIGS. 14-15 illustrate a frame for use in constructing an ear warmer, according to another embodiment of the invention.
Figure 15:
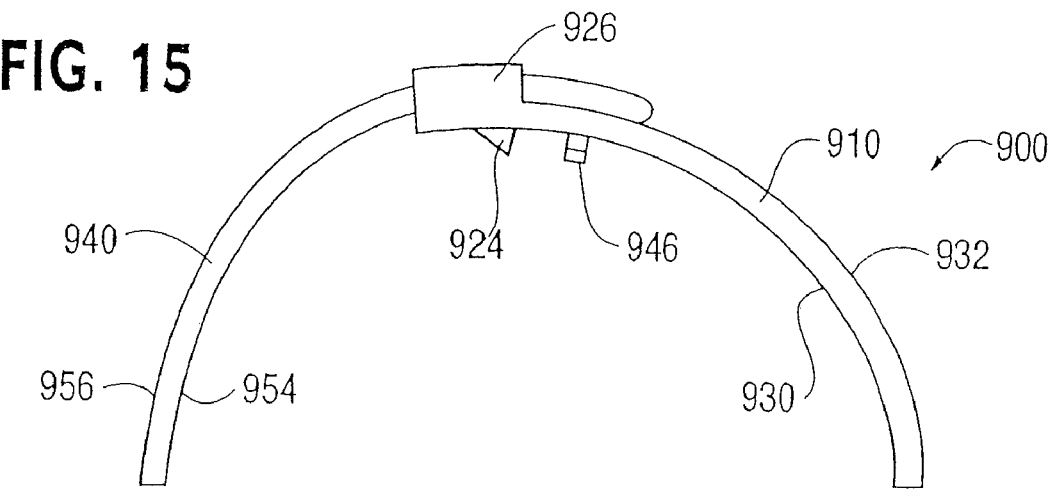

FIG. 14 illustrates a frame for use in constructing an ear warmer, according to another embodiment of the present invention. Frame 900 includes a first frame member or band 910 and a second frame member or band 940 that can be slidably coupled together to form frame 900, as illustrated in FIG. 15.

In the illustrated embodiment, band 910 includes a first end 912 and a second end 914. Band 910 includes curved inner and outer surfaces 930, 932. Band 910 includes an opening 916 proximate to end 912 to which another frame member (not shown in FIG. 14 or 15) may be coupled, as previously discussed. Band 910 also includes a slot 918 extending along the length of the band 910. Slot 918 includes ends 920, 922. In the illustrated embodiment, end 920 is a closed end and end 922 is an open end.

Band 910 includes a passageway 926 located proximate to end 914. Passageway 926 includes an opening 928 through which band 940 may be inserted. A retaining member or abutment 924 is disposed on band 910. Abutment 924 extends a sufficient distance from the surface of the band 910 so that it engages a connecting or locking member disposed on band 940, as discussed in greater detail below. Abutment 924 may be located at any location that enables it to engage the locking member. In one embodiment, abutment 924 is located on the inner surface 930 of band 910. In another embodiment, abutment 924 is located along one of the inner surfaces of the slot 918, and thereby extending into the slot 918. While the abutment 924 is illustrated with a triangular shape, the abutment may have any shape or configuration that can retain the bands 910, 940 together, as discussed below.

In one embodiment, band 940 includes ends 942, 944 and an opening 952 proximate end 944. Band 940 includes inner and outer surfaces 954, 956. Band includes a connecting or locking member 946 on the inner surface 954 proximate to end 942. In this embodiment, locking member 946 includes a shaft 948 and a head 950. Locking member 946 may be formed integral with band 940 or may be coupled thereto. Locking member 946 may be any shape.

In one embodiment, the locking member 946 is fixed relative to band 940. When the frame 900 is assembled, end 942 of band 940 is inserted into passageway 926 of band 910. The band 940 is pushed with sufficient force so that locking member 946 engages abutment 924 and passes over the abutment 924. Abutment 924 may have some flexibility to enable the locking member 946 to pass over it. Once the locking member 946 passes the abutment 924, the bands 910 and 940 can move relative to each other and the locking member 946 engages the abutment 924.

In an alternative embodiment, shaft 948 and head 950 are rotatable relative to the band 940. The locking member 946 can rotate between several positions. In one position, the head 950 of the locking member is oriented substantially parallel to the longitudinal axis of the band 940. This position can be referred to as a locking position. In another position, the head 950 of the locking member may be oriented at an angle with respect to the longitudinal axis of the band 940. The angle may range between 0 and 90°. This position can be referred to as a sliding position.

When the frame 900 is assembled, end 942 of band 940 is inserted into passageway 926 of band 910. Initially, the locking member 946 is rotated to its sliding position. As band 940 slides through passageway 926, the shaft 948 of locking member 946 slides in slot 918. As band 940 is inserted into passageway 926, the locking member 946 passes the abutment 924.

Once the locking member 946 passes the abutment 924, it can be rotated to its locking position, which is illustrated in FIG. 15. In the locking position, head 950 engages abutment 924, thereby retaining bands 910, 940 together. The range of movement of band 940 relative to band 910 while the bands are coupled together is limited to the distance between slot end 920 and abutment 924.

In an alternative embodiment, band 940 can have a hole located where locking member 946 is positioned. In this embodiment, a connector, such as a rivet, can be inserted through the hole and slot 918 to couple the bands 910 and 940 together.

Openings 916 and 952 can be used to couple other frame members (not shown in FIG. 14 or 15) to the frames 910, 940, as discussed above. While the passageway 926 on band 910 and the locking member 946 on band 940 are illustrated on outer surface 932 and inner surface 954, respectively, the passageway 926 and locking member 946 can be located on the opposite sides of each of their respective bands.

Figure 16A:
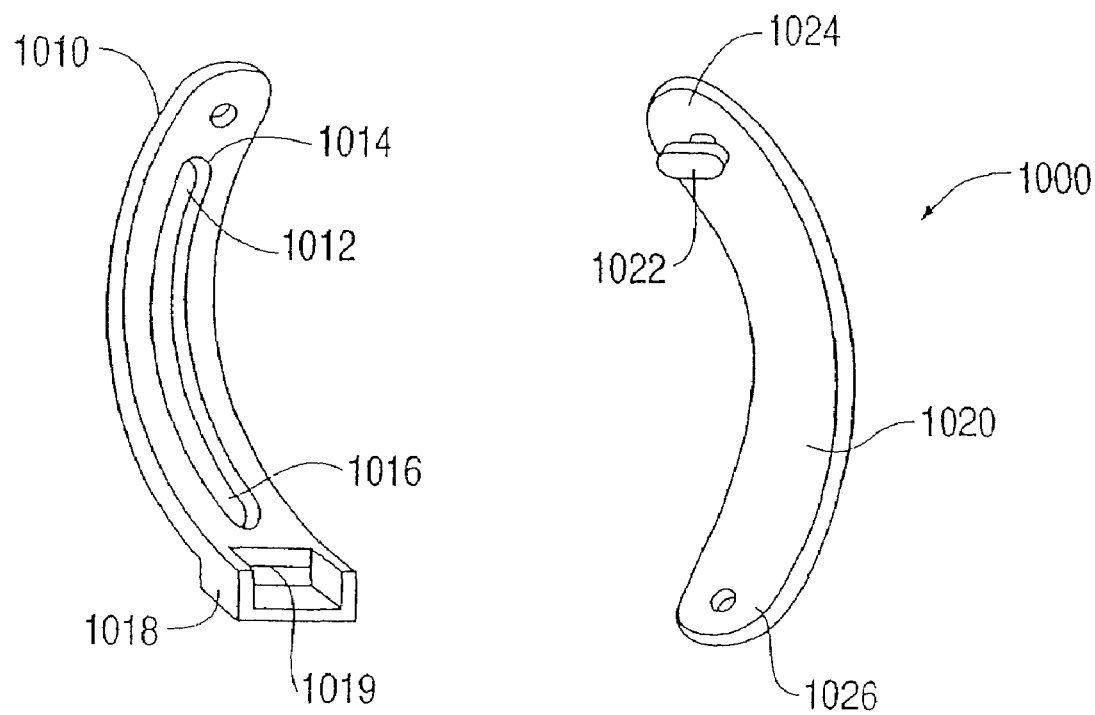
FIGS. 16A-B illustrate a frame for use in constructing an ear warmer, according to another embodiment of the invention.
Figure 16B:
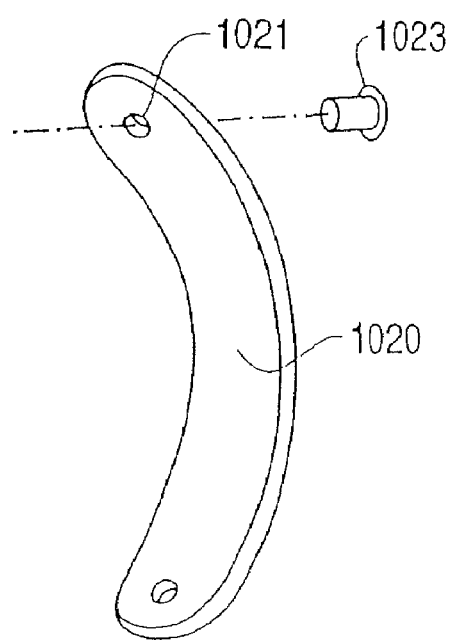

FIGS. 16A-B illustrate other embodiments of a frame for an ear warmer, according to the present invention. In this embodiment, frame 1000 includes bands 1010, 1020 that can be slidably coupled together.

Band 1010 includes a slot 1012 with closed ends 1014, 1016 and a passageway 1018 with an opening 1019 located proximate to an end of the band 1010. In an alternative embodiment, the side surfaces of the slot can be notched.

Band 1020 includes ends 1024, 1026 and a locking member 1022 proximate to end 1024 similar to the locking member 946 described relative to FIGS. 14-15. As discussed relative to locking member 946, locking member 1022 can be either fixed relative to band 1020 or rotatable relative to band 1020.

One method of assembling frame 1000 includes the following steps. Bands 1010, 1020 are placed at an angle to each other and locking member 1022 is inserted into the slot 1012. If the locking member is spherical, then the bands 1010, 1020 can be aligned. Once the locking member 1022 is inserted, the bands 1010, 1020 are turned so that they are substantially parallel to each other. Each of the bands 1010, 1020 is made of flexible material that allows the bands to bend in several directions. Then, end 1026 of band 1020 is inserted into the opening 1019 of passageway 1018. In an alternative embodiment, band 1010 can be longer than band 1020 to facilitate the insertion of end 1026 into opening 1019 and the assembly of the frame 1000.

Bands 1010, 1020 are then slidably coupled together. The range of movement of the bands 1010, 1020 is determined by the length of the slot 1012.

Another method of assembling frame 1000 includes the following steps. Bands 1010, 1020 are placed adjacent each other so that end 1026 is proximate to passageway 1018 and end 1024 is proximate to the other end of band 1010. End 1026 of band 1020 is inserted into the opening 1019 of passageway 1018.

The locking member 1022 is rotated to its sliding position and the head of locking member 1022 is inserted into slot 1012. Because the bands 1010, 1020 are made from a flexible material, such as plastic, band 1020 can be bent during the assembly process to enable locking member 1022 to be inserted into slot 1012. Once locking member 1022 is inserted, locking member 1022 is rotated to its locking position, thereby preventing the separation of bands 1010, 1020. Bands 1010, 1020 are then slidably coupled together. The range of movement of the bands 1010, 1020 is determined by the length of the slot 1012.

In an alternative embodiment, as illustrated in FIG. 16B, the bands can also be coupled together by a connector 1023. Band 1020' includes a hole 1021 through which connector 1023 may be inserted. The use of a connector establishes a non-releasable connection between the bands.

Figure 17:
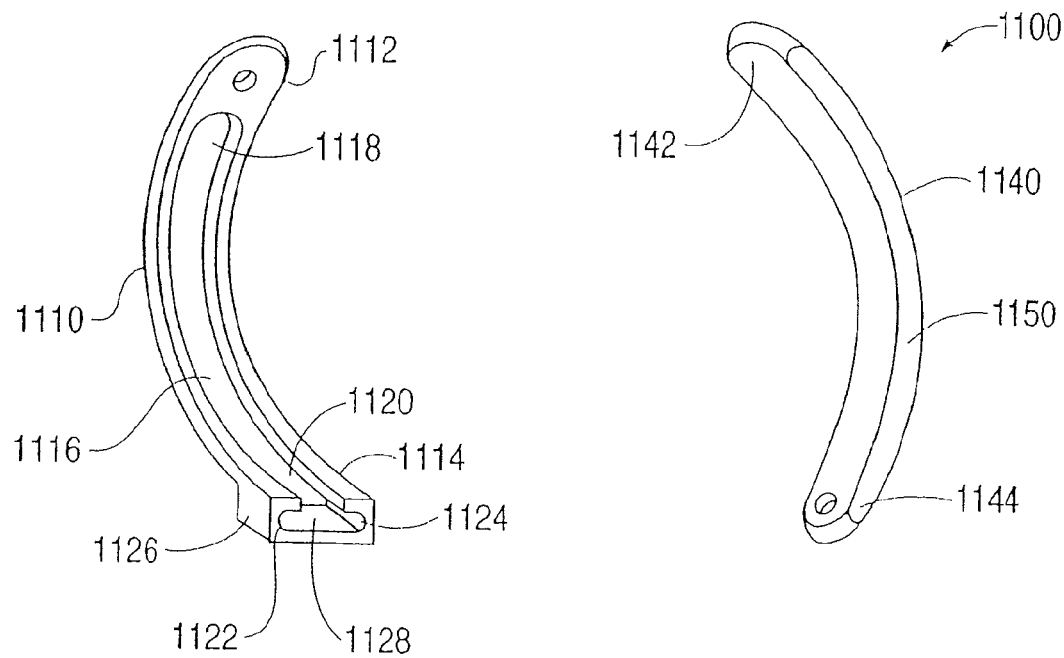
FIGS. 17-20B illustrate a frame for use in constructing an ear warmer, according to another embodiment of the invention.
Figure 18:
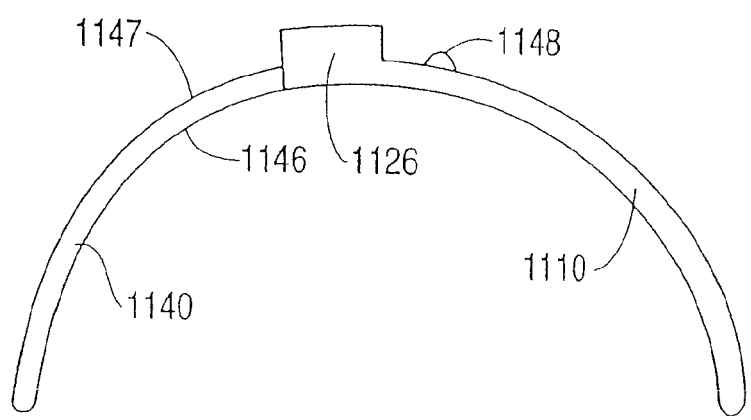

FIGS. 17 and 18 illustrate another embodiment of a frame for an ear warmer, according to the present invention. In this embodiment, frame 1100 includes bands 1110, 1140 that can be slidably coupled together.

Band 1110 includes ends 1112, 1114. Band 1110 also includes a channel 1116 with ends 1118, 1120. In the illustrated embodiment, channel end 1120 is an open end and channel end 1118 is a closed end. Band 1110 also includes a passageway 1126 located proximate to end 1114. Passageway 1126 includes an opening 1128 through which band 1140 can be inserted. Channel 1116 extends substantially along the length of band 1110.

Figure 20A:
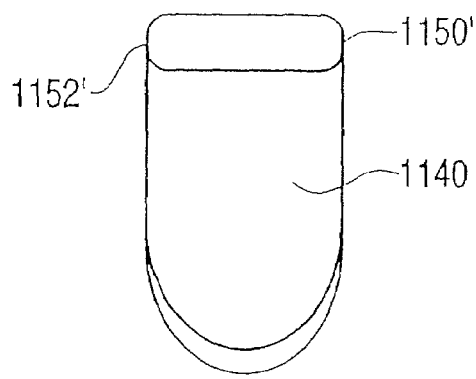
Figure 20B:
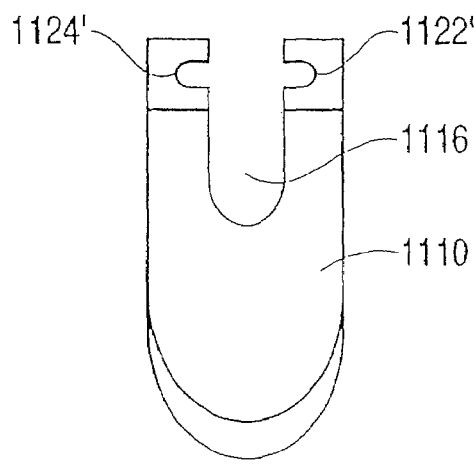

Channel 1116 includes inner side surfaces 1122, 1124 that are curved along their length. In one embodiment, inner side surfaces 1122, 1124 have a convex shape as illustrated in the cross-sectional view shown in FIG. 19B. In an alternative embodiment, inner side surfaces 1122', 1124' have a concave shape as illustrated in the cross-sectional view shown in FIG. 20B.

Band 1140 includes ends 1142, 1144 and inner and outer surfaces 1146, 1147. In one embodiment, a locking nub 1148 is disposed on outer surface 1147, as illustrated in FIG. 18. The locking nub 1148 engages passageway 1126 after the bands 1110, 1140 are coupled together to retain them in a coupled configuration.

Figure 19A:
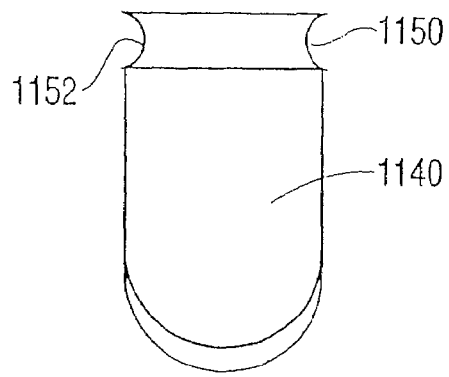
Figure 19B:
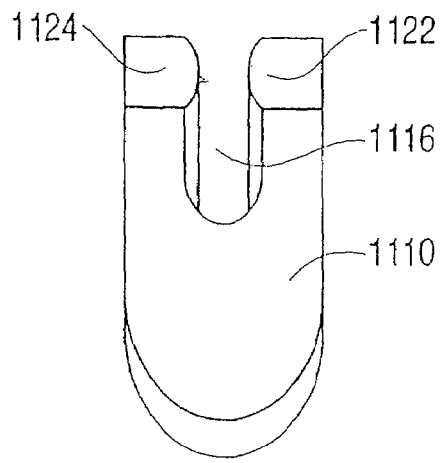

Band 1140 includes side surfaces 1150, 1152 that extend along the length of the band 1140 as illustrated in FIG. 19A. Side surfaces 1150, 1152 are curved along their length. In one embodiment, side surfaces 1150, 1152 have a concave shape as illustrated in the cross-section view shown in FIG. 19A. In an alternative embodiment, side surfaces 1150', 1152' have a convex shape as illustrated in the cross-sectional view shown in FIG. 20A.

As band end 1140 is inserted into channel 1116, side surfaces 1150, 1152 engage inner side surfaces 1122, 1124 on band 1110. The frictional contact between the side surfaces on bands 1110, 1140 provides the necessary force to retain the bands together.

Figure 21:
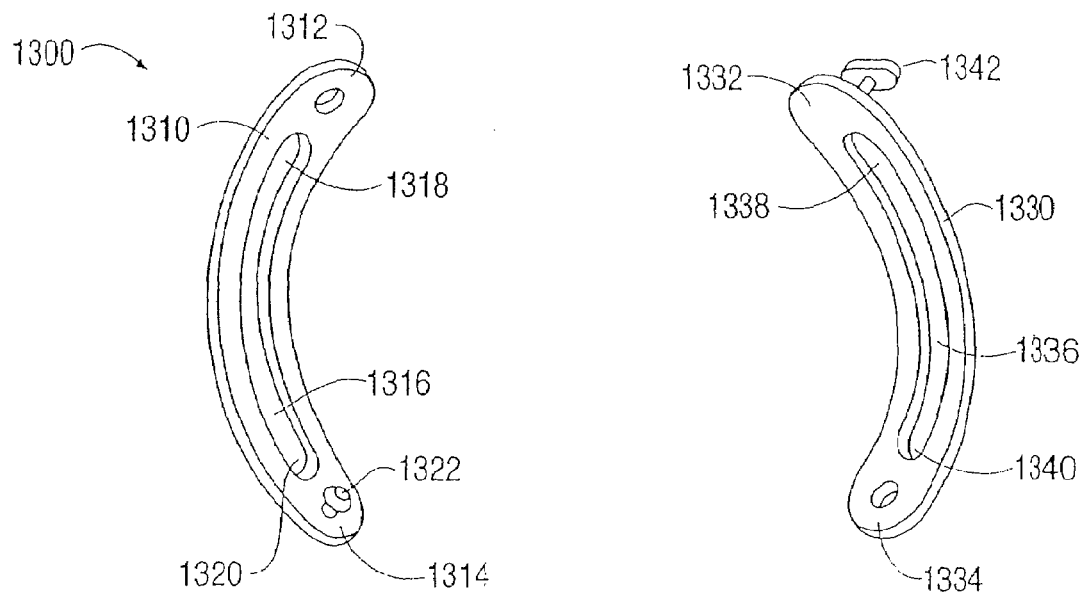
FIGS. 21-23 illustrate a frame for use in constructing an ear warmer, according to another embodiment of the invention.
Figure 22:
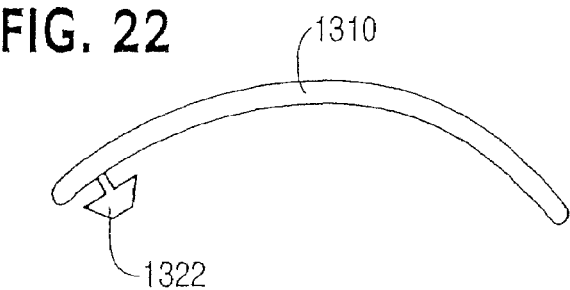

FIG. 21 illustrates another embodiment of a frame for an ear warmer, according to the present invention. Frame 1300 includes bands 1310, 1330 that can be slidably coupled together. Band 1310 includes ends 1312, 1314 and a slot 1316 extending substantially along the length of band 1310. In this embodiment, slot 1316 includes closed ends 1312, 1320. Band 1310 includes a connecting member or retaining member 1322 disposed on its inner surface as illustrated in FIG. 22.

Figure 23:
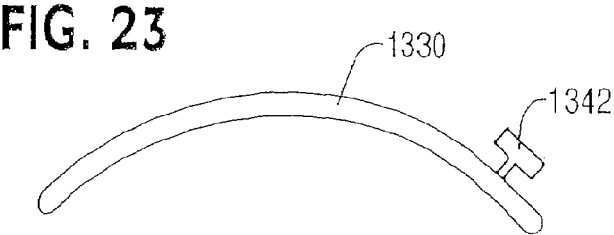

Band 1330 includes ends 1332, 1334 and a slot 1336 extending substantially along the length of band 1330. Slot 1336 includes closed ends 1338, 1340. Band 1330 also includes a locking member 1342 disposed on its outer surface as illustrated in FIG. 23. In one embodiment, locking member 1342 is fixed relative to the band 1330. In another embodiment, locking member 1342 rotates relative to the band 1330.

Frame 1300 is assembled by inserting the locking member 1342 on band 1330 into slot 1316 on band 1310. Depending on the structure of the locking member 1342, band 1310 is turned perpendicular to band 1330 or locking member 1342 is rotated relative to band 1330. Once the locking member 1342 has been inserted, the retaining member 1322 on band 1310 is inserted into slot 1336 of band 1330. At this point, bands 1310, 1330 can slide relative to each other. The movement of bands 1310, 1330 is limited by the length of slots 1316, 1336 and the positions of retaining member 1322 and locking member 1342 on the bands 1310, 1330, respectively.

Retaining member 1322 and locking member 1342 can be any shape that can be inserted into a slot and couple the bands together. Alternatively, connectors, such as rivets, may be used instead of one or both of the retaining member and the locking member to couple the bands.

FIGS. 24 and 25 illustrate a membrane for use in constructing an ear warmer, according to another embodiment of the present invention. Similar to ear membrane 100, ear membrane 110, middle membrane 120, and outer membrane 130 illustrated in FIG. 1, FIGS. 24 and 25 illustrate a shell 1400 having ear membrane 1410, ear membrane 1420, middle membrane 1430, and outer membrane 1440.

One method by which the shell 1400 can be assembled is the following. Ear membrane or portion 1410 can be coupled to one end of the outer membrane or portion 1440. Similarly, ear membrane or portion 1420 can be coupled to the opposite end of outer membrane 1440. Middle membrane or portion 1430 is coupled to the perimeter of outer membrane 1440. The collective perimeter can be sewn, bound, or sewn and the membranes can be turned inside out as described in above in reference to FIGS. 3-5.

In this embodiment, middle portion 1430 includes a coupling mechanism 1460 disposed along one of its edges. The outer portion 1440 includes a similar coupling mechanism 1462 along a portion of its perimeter as illustrated in FIG. 24. Once a frame has been inserted into membrane 1400, the coupling mechanisms 1460, 1462 can be coupled together to secure the middle portion 1430 to the outer portion 1440 and close the interior of the shell 1400.

Coupling mechanisms 1460, 1462 can be any type of fastening mechanism that permanently or releasably couples the middle portion and the outer portion. For example, coupling mechanisms 1460, 1462 can be hook and loop type fasteners. Alternatively, any mechanism that can couple two pieces of fabric together can be used for the coupling mechanisms. Similarly, the middle portion 1430 can be sewn to the outer portion 1440.

Shell 1400 enables a fully-assembled frame to be inserted after the shell is sewn. Shell 1400 also enables shells to be changed on the same frame.

Figure 26:
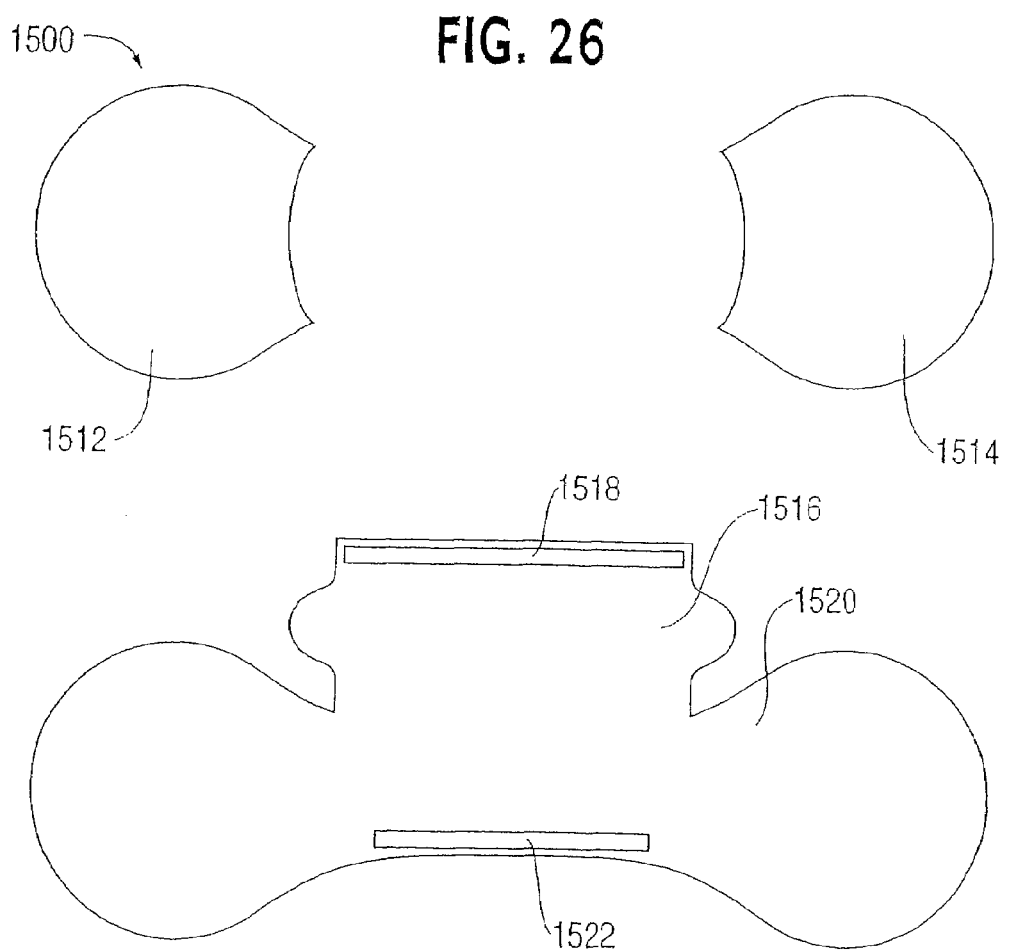
FIG. 26 illustrates a set of membranes for use in constructing an ear warmer, according to another embodiment of the invention.

FIG. 26 illustrates an alternative shell for use in constructing an ear warmer according to another embodiment of the present invention. Membrane 1500 includes ear portions 1512, 1514, and an outer membrane 1520. In the illustrated embodiment, as shown in FIG. 26, middle portion 1516 is integrally formed with the outer membrane 1520. Middle portion 1516 can include a coupling mechanism 1518 located proximate one of its edges.

Outer membrane 1520 includes a coupling mechanism 1522 that can be used with coupling mechanism 1518 on the inner membrane 1510 to secure middle portion 1516 to the outer membrane 1520.

Figure 27:
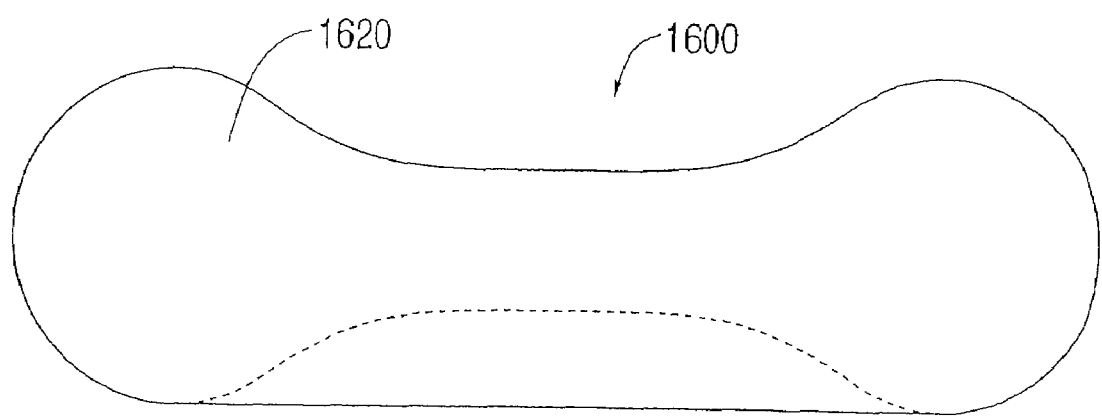
Figure 29:
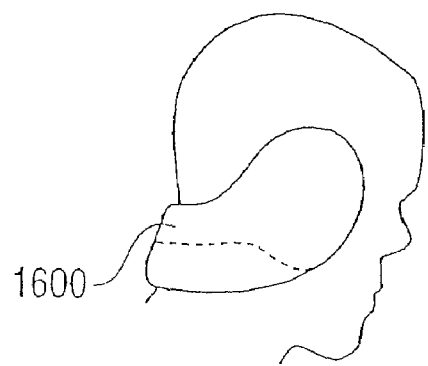

FIGS. 27-29 illustrate an alternative shell for use in constructing an ear warmer, according to an embodiment the present invention. Membrane 1600 includes an inner membrane 1610 and an outer membrane 1620. In this embodiment, inner membrane 1610 has a different shape than outer membrane 1620. Outer membrane 1620 has a thicker middle portion than inner membrane 1610 as illustrated in FIG. 28. Outer membrane 1620 provides additional protection for a neck of a user, as illustrated in FIG. 29.

Figure 30:
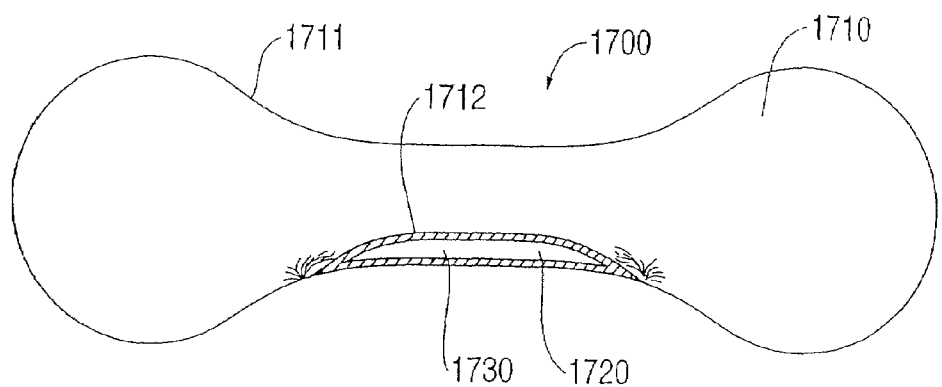
FIG. 30 illustrates a set of membranes for use in constructing an ear warmer, according to another embodiment of the invention.

FIG. 30 illustrates another shell for use in constructing an ear warmer, according to an embodiment of the present invention. Shell 1700 includes an inner membrane 1710 and an outer membrane 1720. Inner membrane 1710 is attached along a portion 1711 of its perimeter to outer membrane 1720 while the remaining portion 1712 of the perimeter of the inner membrane 1710 is not attached to outer membrane 1720. The unattached perimeter portions of inner and outer membranes 1710, 1720 generally correspond to opening 1730 as illustrated in FIG. 30.

A frame for the ear warmer can be inserted through opening 1730 and positioned in the interior region of the shell to support the ear warmer. Once the frame is inserted, opening 1730 can be left open or can be closed by any conventional coupling mechanism, such as sewing, hook and loop fasteners, etc. The frame can be assembled before or after sewing the shell together.

Figure 31:
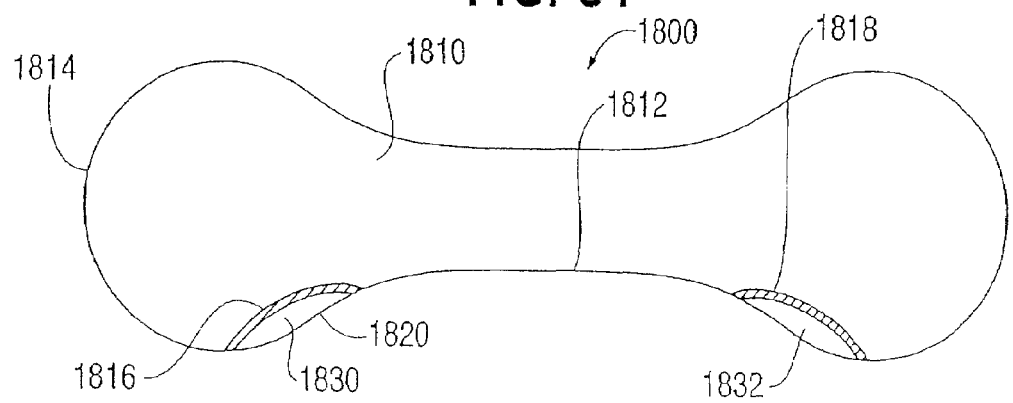
FIG. 31 illustrates a set of membranes for use in constructing an ear warmer, according to another embodiment of the invention.

FIG. 31 illustrates another shell for use in constructing an ear warmer, according to the present invention. Shell 1800 includes an inner membrane 1810 and an outer membrane 1820. The extent that the perimeters of inner and outer membranes 1810, 1820 are coupled together can vary to define one or more openings.

Inner membrane 1810 is attached along two portions 1812, 1814 of its perimeter to outer membrane 1820 while the two remaining portions 1816, 1818 of the perimeter of the inner membrane 1810 are not attached to outer membrane 1820. These unattached perimeter portions 1816, 1818 of inner membrane 1810 generally correspond to openings 1830, 1832, respectively.

A frame can be inserted into one or both of the openings 1830, 1832 and can be subsequently assembled while it is inside the interior region. Openings 1830, 1832 can be left open or be closed using any coupling mechanism.

Figure 32:
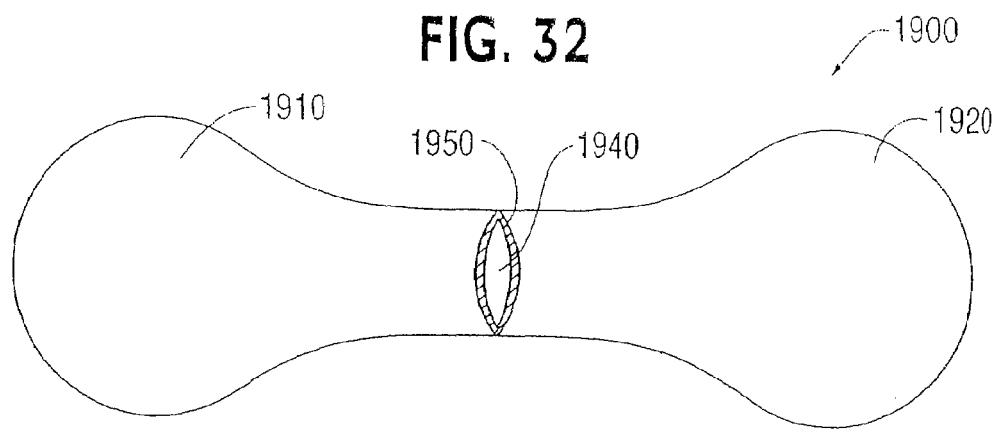
FIGS. 32-33 illustrate a set of membranes for use in constructing an ear warmer, according to another embodiment of the invention.
Figure 33:
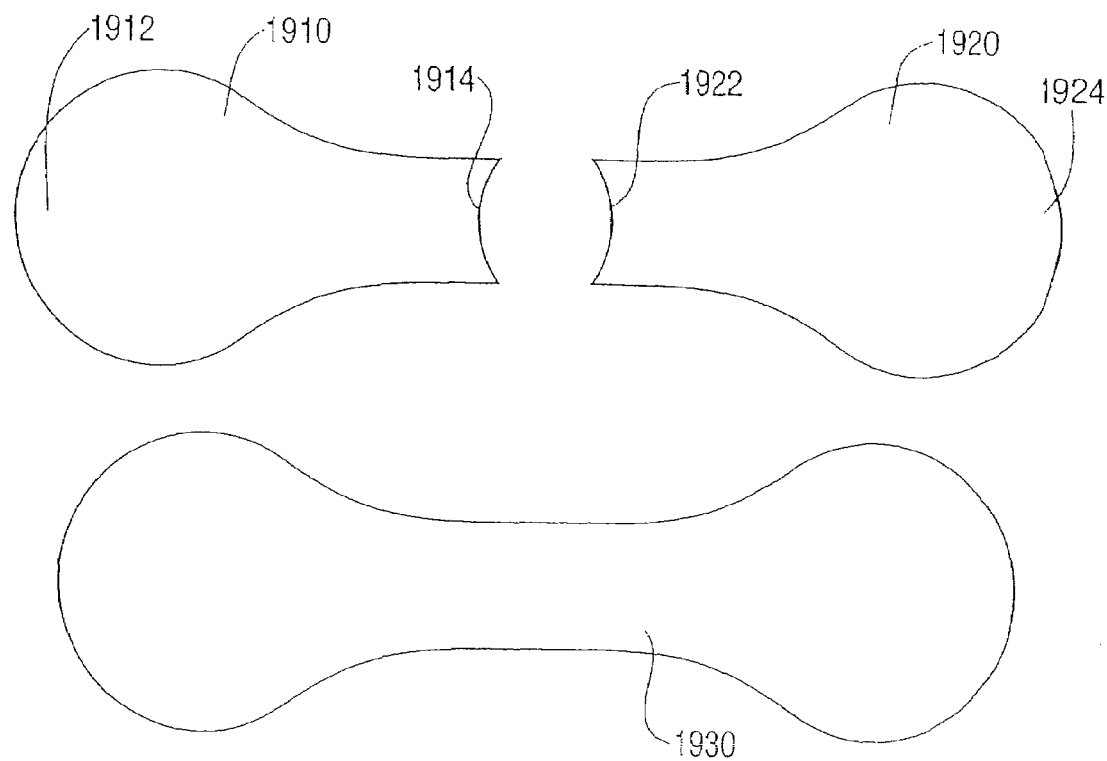

FIGS. 32-33 illustrate a shell for use in constructing an ear warmer, according to the present invention. Shell 1900 includes inner membranes 1910, 1920 and outer membrane 1930. Inner membrane 1910 includes ends 1912, 1914. Similarly, inner membrane 1920 includes ends 1922, 1924. The inner membranes 1910, 1920 function as the ear portions of the shell when the membranes are connected together. The perimeter portions of inner membranes 1910, 1920 can be coupled to the perimeter portion of outer membrane 1930, thereby defining an interior region into which a frame can be inserted.

In one embodiment, ends 1914, 1922 of membranes 1910, 1920 are curved. When membranes 1910, 1920, 1930 are assembled, as illustrated in FIG. 36, an opening 1940 is defined by ends 1914, 1922 which are located proximate to each other. A frame can be inserted into the interior region 1950 of membrane 1900 through opening 1940. Opening 1940 can be left open or can be covered by another piece of material. In one embodiment, the ends 1914 and 1922 contact each other. In another embodiment, the ends 1914 and 1922 may be spaced apart from each other.

It should, of course, be understood that while the present invention has been described in reference to particular configurations, other configurations will be apparent to those of ordinary skill in the art. For example, the membranes and frame members can be made of any type of materials appropriate for an ear warmer device. U.S. Pat. No. 5,835,609, the disclosure of which is incorporated herein by reference, discloses various embodiments of the ear warmer device and those variation can be combined with the method and apparatus described herein.

What is claimed is:

1. An apparatus, comprising:
    an ear warmer shell including:
        a first membrane;
        a second membrane coupled to the first membrane, the second membrane and the first membrane collectively defining an outer perimeter, the second membrane and the first membrane defining therebetween an interior of the ear warmer shell; and
        a third membrane disposed within the interior of the ear warmer shell, the third membrane being coupled to at least one of the first membrane and the second membrane along at least a portion of the outer perimeter; and
    a frame configured to be disposed within the interior of the ear warmer shell, the frame including:
        a band configured to be slidably adjustable, the band having a first end portion and a second end portion, the second end portion being opposite the first end portion;
        a first ear member coupled to the first end portion of the band; and
        a second ear member coupled to the second end portion of the band.

2. The apparatus of claim 1, wherein the band has a first curved member including the first end portion of the band, the band has a second curved member including the second end portion of the band, the second curved member being slidably coupled to the first curved member.

3. The apparatus of claim 1, wherein the band has a first curved member including the first end portion of the band, the band has a second curved member including the second end portion of the band, an end of the first curved member defining a passageway through which the second curved member is disposed to slidably couple the second curved member to the first curved member.

4. The apparatus of claim 1, wherein the first ear member is coupled to the first end portion of the band by at least one rivet; and the second ear member is coupled to the second end portion of the band by at least one rivet.

5. The apparatus of claim 1, wherein the band has a curved portion configured to extend around the back of a user's head,
the first ear member has a portion having a frusto-conical shape, and the second ear member has a portion having a frusto-conical shape.

6. The apparatus of claim 1, wherein the first membrane, the second membrane and the third membrane are coupled together along at least a portion of the outer perimeter by at least one seam; and the ear warmer shell includes a binding disposed about the portion of the outer perimeter, the binding covering the at least one seam.

7. The apparatus of claim 1, wherein at least one of the first membrane, the second membrane and the third membrane is constructed from a fleece.

8. The apparatus of claim 1, wherein an end portion of the first ear member is disposed between a portion of the first membrane and a portion of the third membrane; and an end portion of the second ear member is disposed between a portion of the first membrane and a portion of the third membrane.

9. The apparatus of claim 1, wherein an end portion of the first ear member is disposed between a portion of the second membrane and a portion of the third membrane; and an end portion of the second ear member is disposed between a portion of the second membrane and a portion of the third membrane.

10. An apparatus, comprising:
    an ear warmer shell including:
        an outer membrane;
        an inner membrane coupled to the outer membrane, the inner membrane and the outer membrane collectively defining an interior region therebetween; and
        a cushion membrane, disposed within the interior region, the cushion membrane being coupled to at least the outer membrane; and
    a frame configured to be disposed within the interior region of the ear warmer shell, the frame including:
        a band, the band including a first end portion and a second end portion, the second end portion being opposite the first end portion;
        a first ear member coupled to the first end portion of the band, the first ear member including a frusto-conical portion defining an opening;
        a second ear member coupled to the second end portion of the band, the second ear member including a frusto-conical portion defining an opening.

11. The apparatus of claim 10, wherein the band has a first curved member including the first end portion of the band, the band has a second curved member including the second end portion of the band, an end of the first curved member defining a passageway through which the second curved member is disposed to slidably couple the second curved member to the first curved member.

12. The apparatus of claim 10, wherein the first ear member is coupled to the first end portion of the band by at least one rivet; and the second ear member is coupled to the second end portion of the band by at least one rivet.

13. The apparatus of claim 10, wherein the outer membrane, the inner membrane and the cushion membrane are coupled together along at least a portion of the outer perimeter by at least one seam; and the ear warmer shell includes a binding disposed about the portion of the outer perimeter, the binding covering the at least one seam.

14. The apparatus of claim 10, wherein an end portion of the first ear member is disposed between a portion of the inner membrane and a portion of the cushion membrane; and an end portion of the second ear member is disposed between a portion of the inner membrane and a portion of the cushion membrane.

15. The apparatus of claim 10, wherein an end portion of the first ear member is disposed between a portion of the outer membrane and a portion of the cushion membrane; and an end portion of the second ear member is disposed between a portion of the outer membrane and a portion of the cushion membrane.

16. An apparatus, comprising:

an ear warmer shell including:

a first membrane;

a second membrane coupled to the first membrane, the second membrane and the first membrane collectively defining an outer perimeter, the second membrane and the first membrane defining therebetween an interior of the ear warmer shell; and a third membrane disposed within the interior of the ear warmer shell, the third membrane being coupled to at least one of the first membrane and the second membrane along at least a portion of the outer perimeter; and a frame configured to be disposed within the interior of the ear warmer shell, the frame including:

a band configured to be slidably adjustable, the band having a first end portion and a second end portion, the second end portion being opposite the first end portion;

a first ear member coupled to the first end portion of the band by at least one rivet, the first ear member including a frusto-conical portion defining an opening; and a second ear member coupled to the second end portion of the band by at least one rivet, the second ear member including a frusto-conical portion defining an opening.

17. The apparatus of claim 16, wherein the band has a first curved member including the first end portion of the band, the band has a second curved member including the second end portion of the band, an end of the first curved member defining a passageway through which the second curved member is disposed to slidably couple the second curved member to the first curved member.

18. The apparatus of claim 16, wherein an end portion of the first ear member is disposed between a portion of the first membrane and a portion of the third membrane; and an end portion of the second ear member is disposed between a portion of the first membrane and a portion of the third membrane.

19. The apparatus of claim 16, wherein an end portion of the first ear member is disposed between a portion of the second membrane and a portion of the third membrane, and an end portion of the second ear membrane is disposed between a portion of the second membrane and a portion of the third membrane.

* * * * *